United States Patent [19]
Goll et al.

[11] Patent Number: 5,921,929
[45] Date of Patent: Jul. 13, 1999

[54] ULTRASONIC WAVEFORM ASSAY FOR BONE ASSESSMENT USING VALUES MAPPED OVER A REGION

[75] Inventors: Jeffrey H. Goll, Lake Oswego; Hartwell H. Whitney, Portland, both of Oreg.

[73] Assignee: Metra Biosystems, Inc., Mountain View, Calif.

[21] Appl. No.: 08/938,101

[22] Filed: Sep. 26, 1997

Related U.S. Application Data

[60] Provisional application No. 60/026,815, Sep. 27, 1996.

[51] Int. Cl.⁶ .......................................... A61B 8/00
[52] U.S. Cl. .......................... 600/438; 600/442
[58] Field of Search .................... 600/447, 449, 600/442, 438; 607/122

[56] References Cited

U.S. PATENT DOCUMENTS

| | | | |
|---|---|---|---|
| 4,105,018 | 8/1978 | Greenleaf et al. | 128/2 V |
| 4,361,154 | 11/1982 | Pratt, Jr. | 128/660 |
| 4,669,482 | 6/1987 | Ophir | 128/660 |
| 4,941,474 | 7/1990 | Pratt, Jr. | 128/660.01 |
| 5,042,489 | 8/1991 | Wiener et al. | 128/661.03 |
| 5,259,384 | 11/1993 | Kaufman et al. | 128/660.01 |
| 5,480,422 | 1/1996 | Ben-Haim | 607/122 |
| 5,483,965 | 1/1996 | Wiener et al. | 128/661.03 |
| 5,592,943 | 1/1997 | Buhler et al | 128/661.03 |
| 5,720,290 | 2/1998 | Buhler et al. | 128/661.03 |
| 5,840,029 | 11/1998 | Mazess et al. | 600/437 |

FOREIGN PATENT DOCUMENTS

| | | |
|---|---|---|
| 0 737 441 A1 | 10/1996 | European Pat. Off. . |
| PCT/EP96/05030 | of 0000 | WIPO . |
| WO 96/33657 | 10/1996 | WIPO . |
| WO 97/18756 | 5/1997 | WIPO . |

OTHER PUBLICATIONS

Laugier et al. "Ultrasound Images of the OS Calcis: A New Method of Assessment of Bone Status," Proceedings IEEE, 1993 Ultrasonics Symposium, vol. 2, Oct. 31, 1993–Nov. 3, 1993, pp. 989–992.

Mahrt et al. "Extremely Sensitive Ultrasound Scanning System for Non–Invasive In Vivo Detection of Minute Mineralisation Changes in Human Heel Bones," Proceedings IEEE 1991 Ultrasonics Symposium, vol. 2, Dec. 8–11, 1991, US, pp. 1119–1122.

Laugier et al., Ultrasound Images of the Os Calcis: a New Method of Assessment of Bone Status, Proceedings IEEE 1993 Ultrasonics Symposium, vol. 2, pp. 989–992, Oct. 31, 1993.

*Primary Examiner*—Marvin M. Lateef
*Assistant Examiner*—Ali M. Imam
*Attorney, Agent, or Firm*—Bromberg & Sunstein LLP

[57] ABSTRACT

An apparatus and methods determine externally in a vertebrate subject the porosity and non-connectivity of a bone. A preferred embodiment has an acoustic transceiver with a pair of acoustic transducers disposed in a specified spatial relationship with one another, such that an acoustic signal is transmitted from one to another via the bone. The transmission path through the bone corresponding to the acoustic signal analyzed by the system may be varied, with values derived from measures of acoustic transmission through differing locations in the bone stored in different locations of a memory. A location processor is provided for selecting a target location based at least in part on the values stored in the memory for defining a region of interest with respect to which a measure of bone porosity is determined.

20 Claims, 30 Drawing Sheets

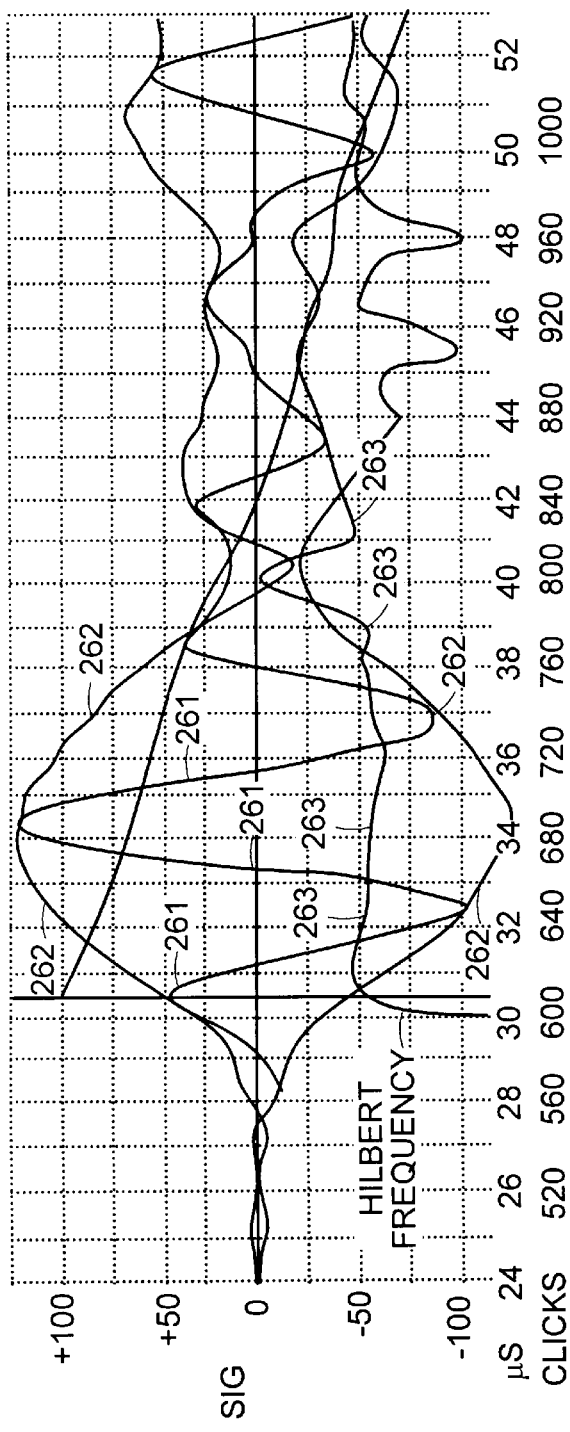
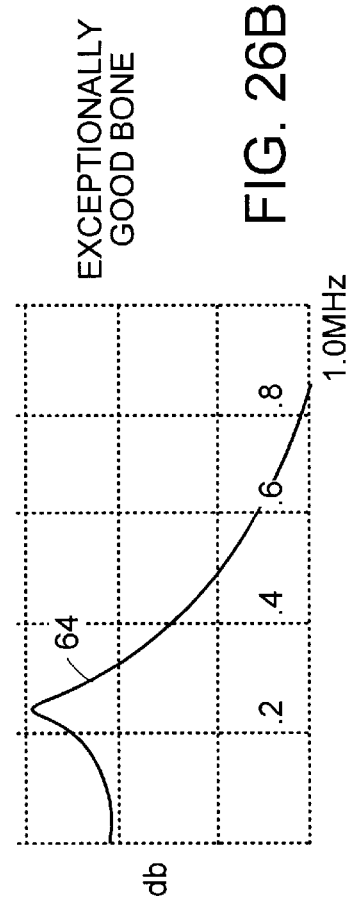
FIG. 26A
FIG. 26B

ULTRASONIC WAVEFORM ASSAY FOR BONE ASSESSMENT USING VALUES MAPPED OVER A REGION

The present application claims priority from U.S. provisional application number 60/026,815, filed Sep. 27, 1996, which is herein incorporated by reference.

TECHNICAL FIELD

The present invention relates to apparatus and methods for the acoustic analysis of bone, and more particularly to apparatus and methods for accomplishing bone measurement using signal processing techniques in temporal, frequency, and spatial domains.

BACKGROUND ART

The prior art is rich with approaches to measurement of bone characteristics using acoustic and other methods with a view to identifying patients in need of treatment for bone conditions and diseases. Many acoustic techniques utilize a first transducer to provide an acoustic signal, typically at ultrasonic frequencies, to the subject from a first external location and a second transducer at a second external location disposed on the opposite side of the bone of interest to receive the signal transmitted by the first transducer through the bone and intervening soft tissue. (The transducers are typically coupled to the subject through a suitable fluid, such as water or water gel.) It is common to use an arrangement of transducers with a circuit to estimate the speed of an acoustic wave through bone. The estimated speed is correlated with bone condition. Under another approach, there is determined the Broadband Ultrasound Attenuation (BUA) in the range of approximately 300 to 700 kHz. The BUA is defined as the slope of a linear logarithmic-amplitude versus frequency plot of the energy transmitted through the heel. Determinations of acoustic wave speed or BUA through bone may also be made at a plurality of locations to improve the methodology, but these approaches have not provided the desired level of specificity and sensitivity.

SUMMARY OF THE INVENTION

In a preferred embodiment, the invention provides an apparatus for externally determining in a vertebrate subject an index of porosity and non-connectivity of bone disposed within a body part. The apparatus includes an acoustic transceiver that has a signal generator for producing, when coupled to a transducer, an acoustic pulse, having energy distributed over a frequency range. The transceiver also has a transducer assembly including a plurality of transducers and providing a pair of transducers in spaced relationship with respect to the bone. A first one of the pair of transducers is coupled to the signal generator so as to provide an acoustic pulse and a second one of the pair receives an acoustic signal resulting from propagation of the acoustic pulse along a path that includes the bone. The assembly is configured so that the path may be disposed in a plurality of positions so as to pass through a plurality of locations within a selected region of the bone.

A signal processor is in communication with the second one of the pair of transducers. The signal processor provides a measure, associated with each of the locations, that is indicative of at least one of spectral or temporal components of a portion, up to the whole amount thereof, of the signal received by the second one of the pair of transducers. The signal processor operates in communication with a value memory for storing the values related to the measure associated with the locations. A location processor selects a target location based at least in part on the values stored in the value memory, and an output processor provides as an output a quantity associated with the target location or with a topological signature of a spatial distribution of the measure in the selected region of the bone.

BRIEF DESCRIPTION OF THE DRAWINGS

The invention will be more readily understood by reference to the following drawings, taken with the accompanying detailed description, in which:

FIG. 26A provides a plot showing the stored output of transducer $T_R$ of FIG. 1 in response to an excitation waveform, generated by the system of FIG. 1 and transmitted through an exceptionally healthy bone, as well as plots pertinent to calculation of UBIs in accordance with a preferred embodiment of the invention;

FIG. 26B provides a plot of the Burg spectral estimation function associated with plots of FIG. 26A;

DETAILED DESCRIPTION OF SPECIFIC EMBODIMENTS

In United States patent application (the "Prior Application") Ser. No. 08/615,643, filed Mar. 13, 1996, and allowed Aug. 26, 1997, for an invention entitled "Apparatus and Method for Acoustic Analysis of Bone Using Optimized Functions of Spectral and Temporal Signal Components", a copy of which is attached hereto and incorporated herein by reference as Exhibit A, there is disclosed a system with which the present invention may be employed.

1. General Arrangements, Signal Generation, and Signal Processing

Figure 1:
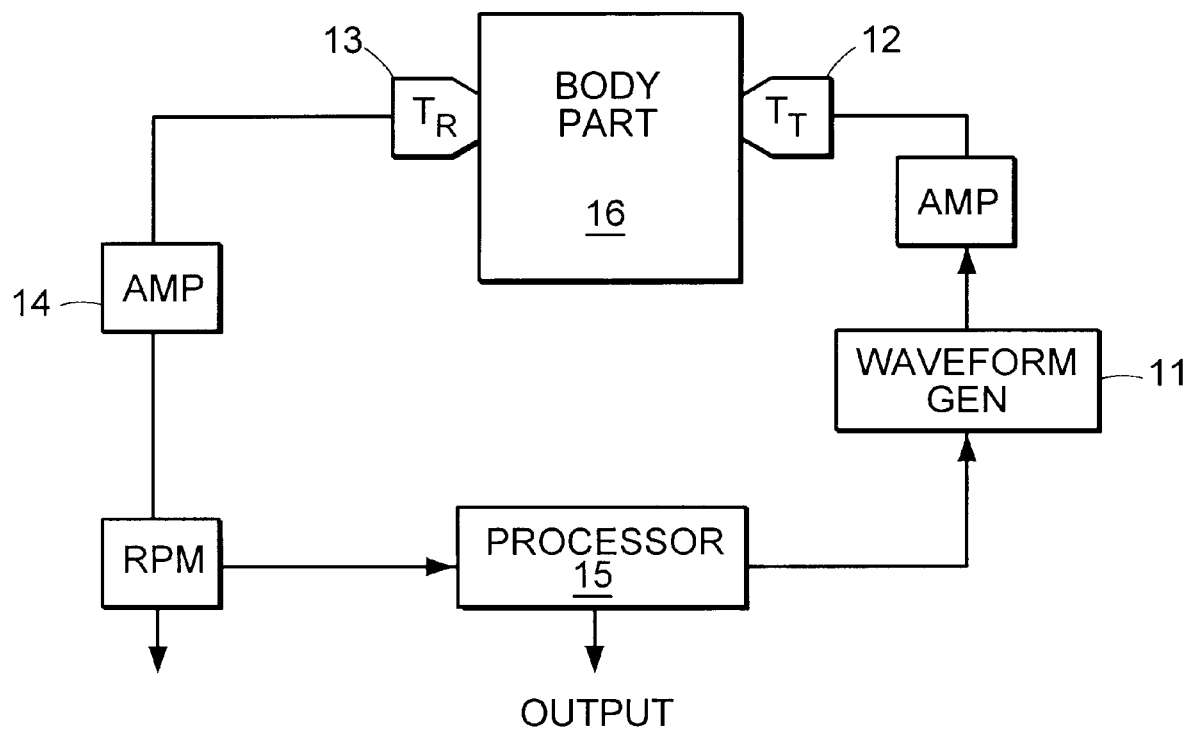
FIG. 1 is a diagram showing in general the components for a system for use in accordance with a preferred embodiment of the invention.

FIG. 1 is a diagram showing in general the components for a system of the type described in the Prior Application and that may be used in accordance with a preferred embodiment of the present invention. In this system, a waveform is generated by waveform generator 11, and delivered to transmitting transducer $T_T$, item 12. Transducer $T_T$ is acoustically coupled to body part 16 of a subject and produces an acoustic wave that is propagated into body part 16 and in particular into a bone within the body part. The transducer $T_R$, item 13, is also acoustically coupled to body part 16 and receives a signal resulting from the effects, among other things, of propagation of the acoustic wave through the bone and the body part. Any components for transmitting and receiving an acoustic signal via a body part are referred to collectively as an "acoustic transceiver" in this description and in the appended claims. The output of the transducer $T_R$ is amplified by amplifier 14 and processed by processor 15. Processor 15 analyzes the output of the transducer $T_R$, and may make a determination reflective of the condition of the bone, and provides an output.

Figure 2:
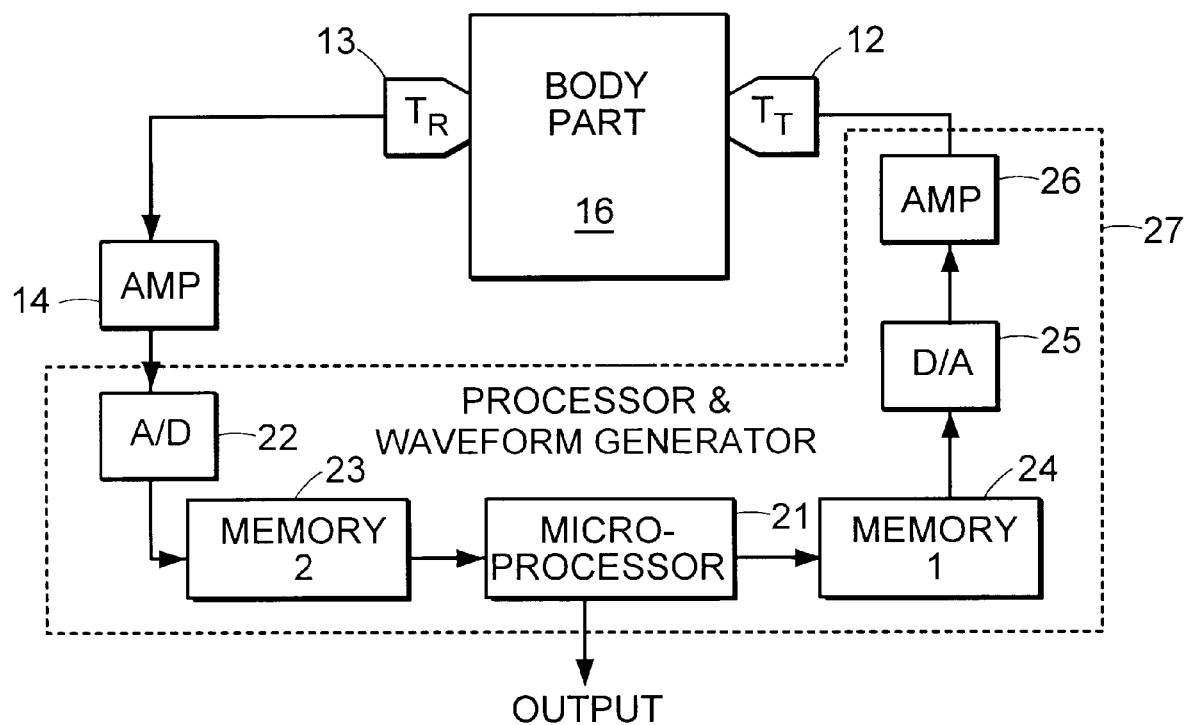
FIG. 2 is a diagram showing an implementation of the system of FIG. 1.

FIG. 2 is a diagram showing an implementation of the system of FIG. 1. The body part may be, for example, the region proximate to the calcaneus. While the elements of FIG. 1 may be implemented in analog components, in a manner known in the art, it is convenient to use a digital implementation. Accordingly, processor 15 and waveform generator 11 may be realized in a unit 27 including a microprocessor 21 that controls both processing of the output from the transducer $T_R$ and the generation of the waveform used for exciting transducer $T_T$. This waveform is stored in digitized form in memory 1, item 24, and under control of microprocessor 21 is run through digital-to-analog converter 25 before being provided to amplifier 26 and the transducer $T_T$. Similarly, the output of receiving transducer $T_R$ is fed from amplifier 14 to analog-to-digital converter 22 and this digitized output is stored in memory 2, item 23. The stored output is then processed by microprocessor 21, which provides a data output indicating the condition of the bone.

In further embodiments of the system, the embodiments of FIG. 2 (or a wholly or partially analog implementation of FIG. 1) are used to process the stored output of $T_R$ in accordance with any one or more of a variety of procedures to provide a data output indicating the condition of the bone. In accordance with some embodiments, the data output indicating bone condition includes a number, which we call the "Ultrasonic Bone Index" (UBI). Each different procedure we employ can lead to a different UBI, and the various UBI types are identified by a numerical suffix, for example, UBI-2, UBI-3, etc. The procedures for UBI-2 through UBI-8 are described in detail in the Prior Application. In connection with the general signal processing techniques utilized (but not their specific utilization in the context of ultrasonic bone testing), the following references are pertinent: Boualem Boashash, ed., *Time-Frequency Signal Analysis* (Wiley, 1992)(especially pertinent to instantaneous frequency analysis; see especially ch. 2, pages 43–73) and Richard Shiavi, *Introduction to Applied Statistical Signal Analysis* (Irwin, 1991)(especially pertinent to Burg Spectral Estimation; see especially pages 369–373). These texts are hereby incorporated herein by reference.

The procedures take advantage of the fact that relatively nonporous and connective bone, on the one hand, and relatively porous and non-connective bone, on the other hand, respond differently to ultrasound inputs. The various UBIs described in the Prior Application are relevant to the present invention and are described below.

UBI-2. In accordance with UBI-2, the stored output of $T_R$ is run through a discrete Fourier transform. A weighted linear sum of the logarithm of resulting frequency components is then computed; this sum is UBI-2. The weights are chosen to minimize differences among successive measurements taken of the same individual and to maximize differences in measurements taken of different individuals, so that the function acts as a discriminant in determining the extent of non-connectivity and porosity of bone.

UBI-3. The UBI-3 procedure utilizes the Hilbert envelope of the stored output of $T_R$; the Hilbert envelope provides a measure of the energy content of the received waveform as a function of time. The greater preponderance of low frequency signals in the received waveform associated with healthy bone causes it to have a longer duration than in the received waveform associated with relatively porous bone. Accordingly, in accordance with UBI-3, the Hilbert envelope is examined for energy duration.

UBI-4. The UBI-4 procedure utilizes an autoregressive moving average (ARMA) spectral estimation function of the stored output $T_R$. In one embodiment, UBI-4 uses the Burg spectral estimation function of the stored output of $T_R$; the Burg function provides a plot estimating power versus frequency of the received waveform. The shape of the plot is a discriminant between healthy and relatively porous bone. UBI-4 is an estimate of the slope (in dB/MHZ) of the log (sdf) vs. f function. Generally the more steeply negative the slope, the healthier the bone. UBI-4b is an estimate of the slope made by reference solely to two points on the plot, the first occurring at the first peak, and the second occurring 400 kHz higher in frequency.

Figure 24A:
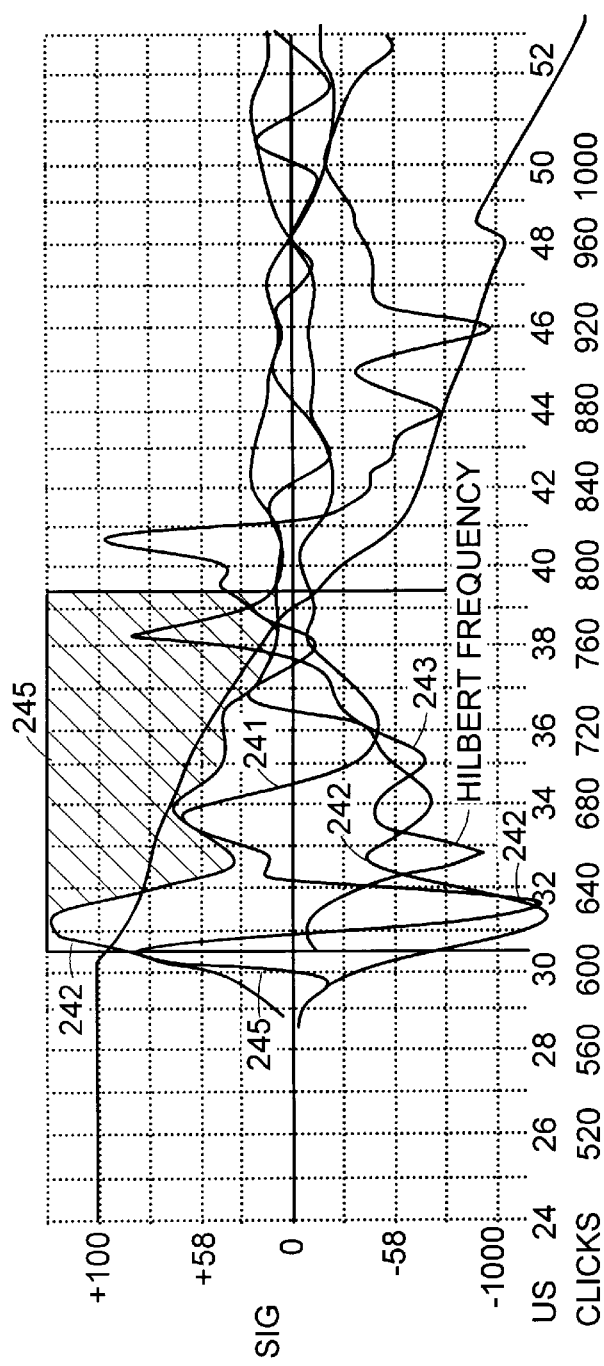
FIG. 24A provides a plot showing the stored output of transducer $T_R$ of FIG. 1 in response to an excitation waveform, generated by the system of FIG. 1 and transmitted through a bone having substantial porosity, as well as plots pertinent to calculation of UBIs in accordance with a preferred embodiment of the invention.
Figure 24B:
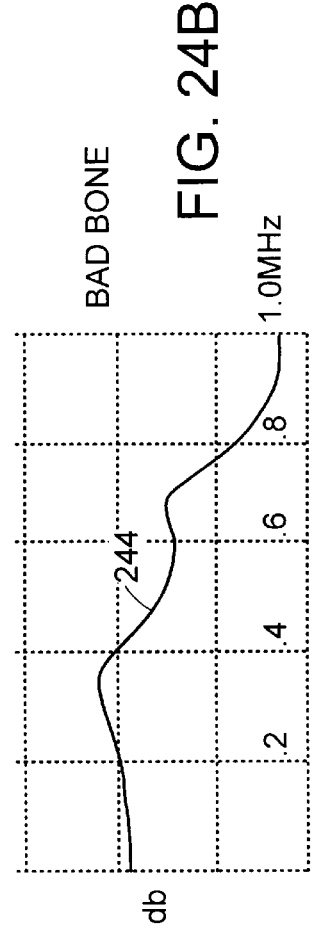
FIG. 24B provides a plot of the Burg spectral estimation function associated with plots of FIG. 24A.
Figure 25A:
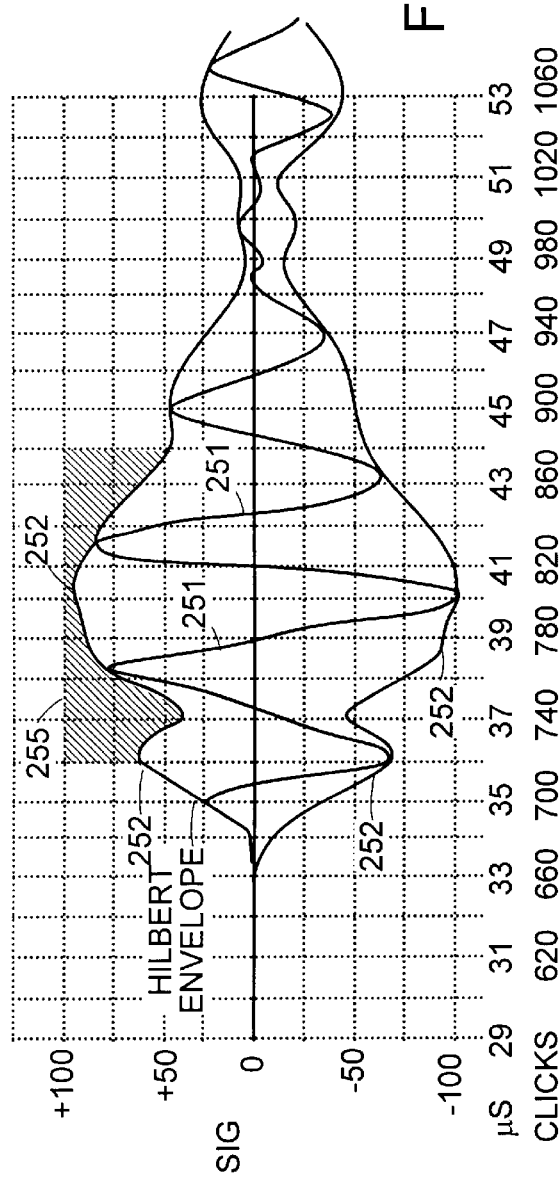
FIG. 25A provides a plot showing the stored output of transducer $T_R$ of FIG. 1 in response to an excitation waveform, generated by the system of FIG. 1 and transmitted through a bone of low-normal quality, as well as plots pertinent to calculation of UBIs in accordance with a preferred embodiment of the invention.
Figure 25B:
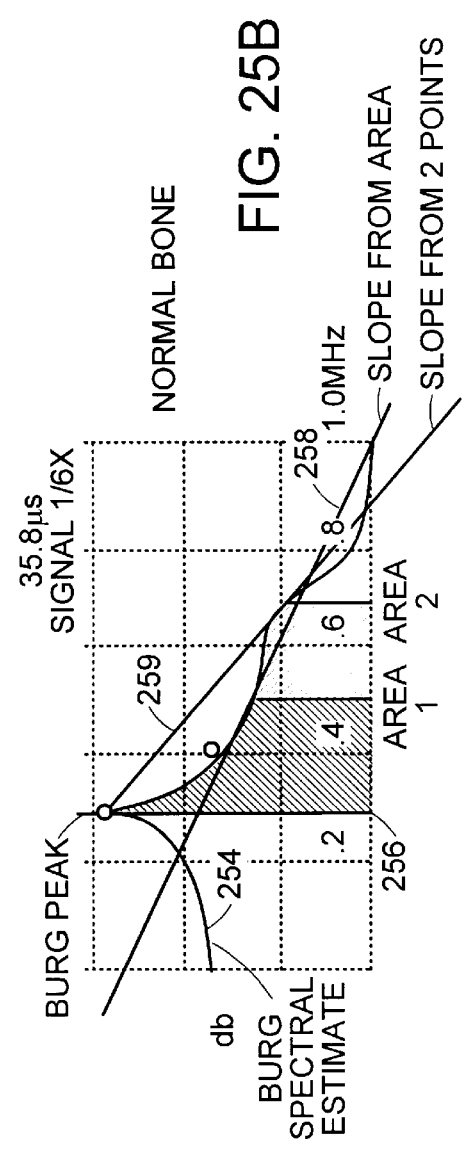
FIG. 25B provides a plot of the Burg spectral estimation function associated with plots of FIG. 25A.

UBI-5. The UBI-5 procedure utilizes a measure related to the instantaneous frequency during the early portion of the received waveform. One embodiment utilizes the Hilbert frequency function. The early portion of the received waveform may be more representative of the body part, and, particularly, of the bone, under analysis in that it is not contaminated by acoustic transmission between the transmitting and receiving transducers via multiple paths. Analysis based on the early portion of the received waveform is discussed with reference to FIGS. 24A–B, FIGS. 25A–B, and FIGS. 26A–B. FIG. 24 As taught, for example, by Boashash, a signal may be represented generally in the form:

$$f(t)=a(t)e^{i\phi(t)}. \quad (1)$$

It is well known in the art that a(t) represents the envelope of the signal, and that $\phi(t)$ is the frequency function of the signal. In particular, where the decomposition of the functional behavior of the signal is made into the form of Eqn. (1) using the Hilbert transform (Boashash, at page 26), such as is appropriate where the signal predominantly tracks the central frequency of the excitation source, then the envelope, a(t), may be referred to as the Hilbert envelope and the frequency function may be referred to as the Hilbert frequency function. Both the envelope and frequency function vary as a function of time, due both to the transient nature of the excitation and the nature of the bone response, and their values, for the respective cases of diseased and healthy bone, are represented by numerals 242 and 243 in FIG. 24A and numerals 262 and 263 in FIG. 26A. For healthy bone, during the early portion (3 or 4 microseconds) of the received waveform, there is little variability and the dominant frequency is relatively low. For relatively porous bone, there is considerable variability and the dominant frequency is relatively high. The variability can be quantified according to any of a variety of methods well-known in the art. As an alternative, or in addition, to measuring the variability of the Hilbert frequency function with time, it is possible to determine the dominant frequency in a prescribed early subsection of the received burst; bad bone has a dramatically higher dominant frequency in this region. We refer to the dominant frequency and period during this time interval as the "Dominant Early Frequency" and "Dominant Early Period," respectively. One way of making this frequency or period determination is to calculate the Hilbert function in this region and then determine the average slope of the Hilbert phase vs. time plot over the interval. Alternatively, a measure of the dominant frequency in this region can be estimated directly from sample wave form data with good success. The UBI-5c index is an estimation of the period utilizing two points lying on each side of the first substantial peak. The two points in this embodiment are determined as the locations (the "inflection points") where the second derivative with respect to time is zero. The half-period is estimated as the duration between the intercepts of tangents to the curve at these two points. The UBI-5c value is the corresponding full period in microseconds. Alternate embodiments employ other measures of the early dominant frequency. These may include, but are not limited to, measurement of the peak-to-trough interval or peak-to-zero separation of the first half cycle, or determination of the slope of the received signal at the second zero crossing.

UBI-6. The UBI-6 procedure utilizes the short-time Fourier transform of the stored output of $T_R$ to examine in more detail than with the Hilbert transform the varying spectral content of the received waveform over time. A frequency index may be computed in a fashion analogous UBI-2. The temporal variation of this index may be used to compute a different index in a fashion analogous to UBI-5.

UBI-7. The UBI-7 procedure utilizes the Fourier transform of the stored output of $T_R$ to produce data permitting a plot of phase versus frequency; the slope of this plot is a measure of velocity (as a function of frequency). The variation of velocity (or its time domain counterpart, group delay) with frequency is dispersion, which can be quantified according to any of a variety of methods. In relatively porous bone, there is relatively little dispersion; in relatively nonporous bone, there is relatively more dispersion.

UBI-8. The UBI-8 procedure is premised on the recognition that bad bone produces a broad band signature, whereas good bone tends to pass relatively low frequencies more selectively. Accordingly, UBI-8 involves the determination of (i) "narrow-band energy," which, for the purposes of this description and the following claims, is the energy associated with 100 kHz of spectrum surrounding the low-frequency spectral peak, and (ii) "broad-band energy," which, for the purposes of this description and the following claims, is the energy associated with the full spectrum of 0–1000 kHz. UBI-8 is the normalized ratio of narrow-band energy to broad-band energy.

As described in the Prior Application, the foregoing UBIs are merely illustrative; other UBIs or combinations of UBIs may be utilized.

2. Location Analysis

Spatial plots of the various measures of bone integrity, such as the foregoing UBIs, or others, may be obtained and displayed, as shown in the surface plots of FIGS. 3–10, or in the topographical plots of FIGS. 11–18, or in any other representation employing a gray-scale or one or more colors, wherein a measure or combination of measures of bone integrity is plotted as a function of position with respect to the bone of the subject.

Spatial mapping may be achieved by any means of deriving ultrasound diagnostic information at a plurality of positions with respect to the bone of the subject. These may include, without limitation, scanning the acoustic transceiver either mechanically or electronically with respect to the bone. Spatial mapping, in accordance with various embodiments of the present invention, may be employed advantageously for a variety of purposes, including without limitation:

(a) defining one or more 'regions of interest' with respect to definable features of the bone of the subject, such as the edge or edges of the bone, which regions are of particular diagnostic utility;

(b) defining one or more 'regions of interest' with respect to definable features of the topology of the diagnostic measure itself, thus, for example, a specified region surrounding a minimum with respect to a particular UBI parameter, where such a region is known to be of particular diagnostic utility;

(c) determining the on-bone/off-bone transition, i.e., the edge of the bone, for use in defining regions of particular diagnostic utility: and (d) employing topological signatures or geometrical features of the spatial map itself as one or more diagnostic measures. Thus, for example, the curvature of a particular UBI field, as a spatial function, may be employed, in accordance with an embodiment of the present invention, for diagnostic purposes.

Figure 3:
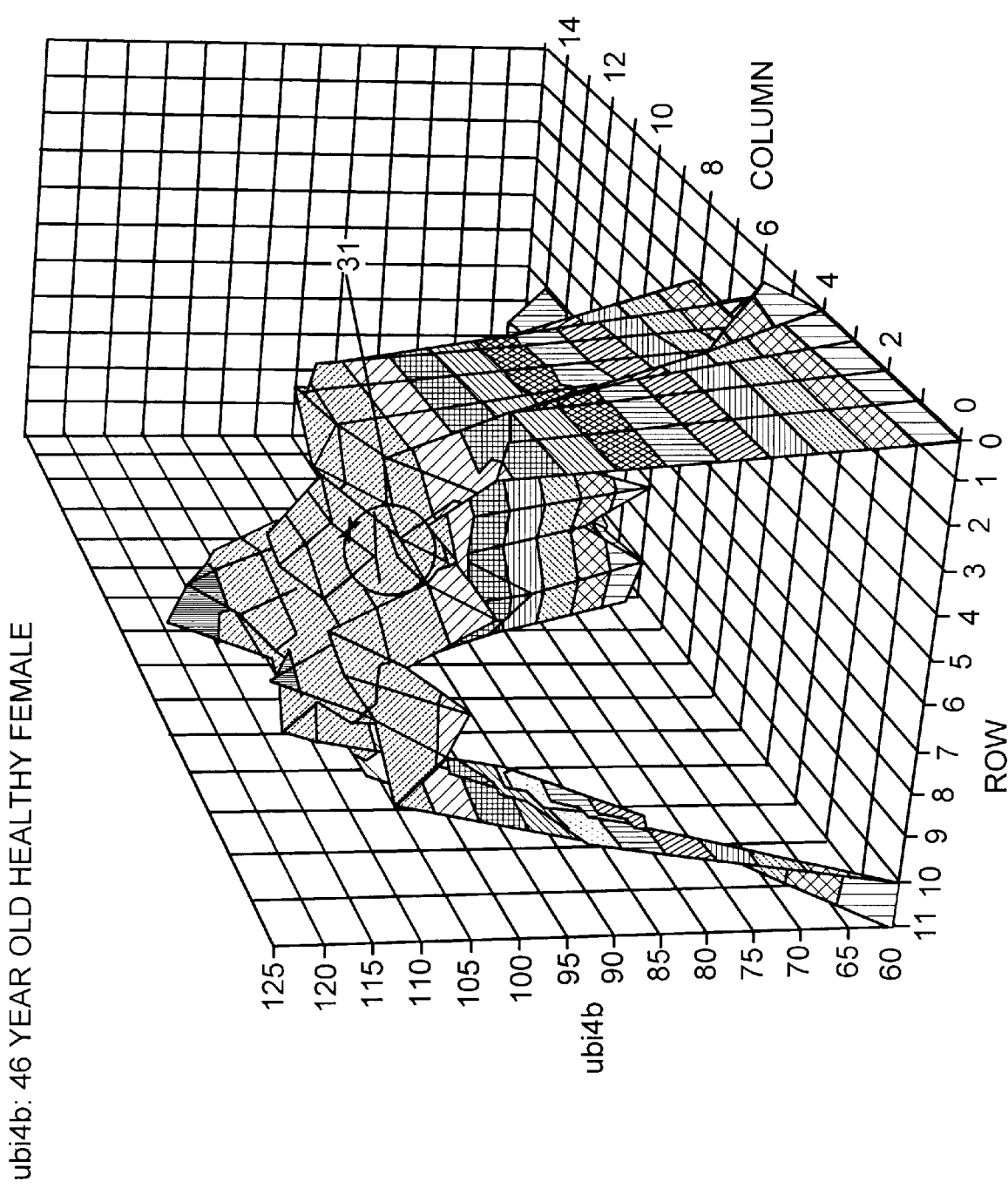
FIGS. 3 and 4 are surface plots of UBI-4b and UBI-5c respectively over a two-dimensional region of the calcaneus of a 46-year old healthy female.
Figure 4:
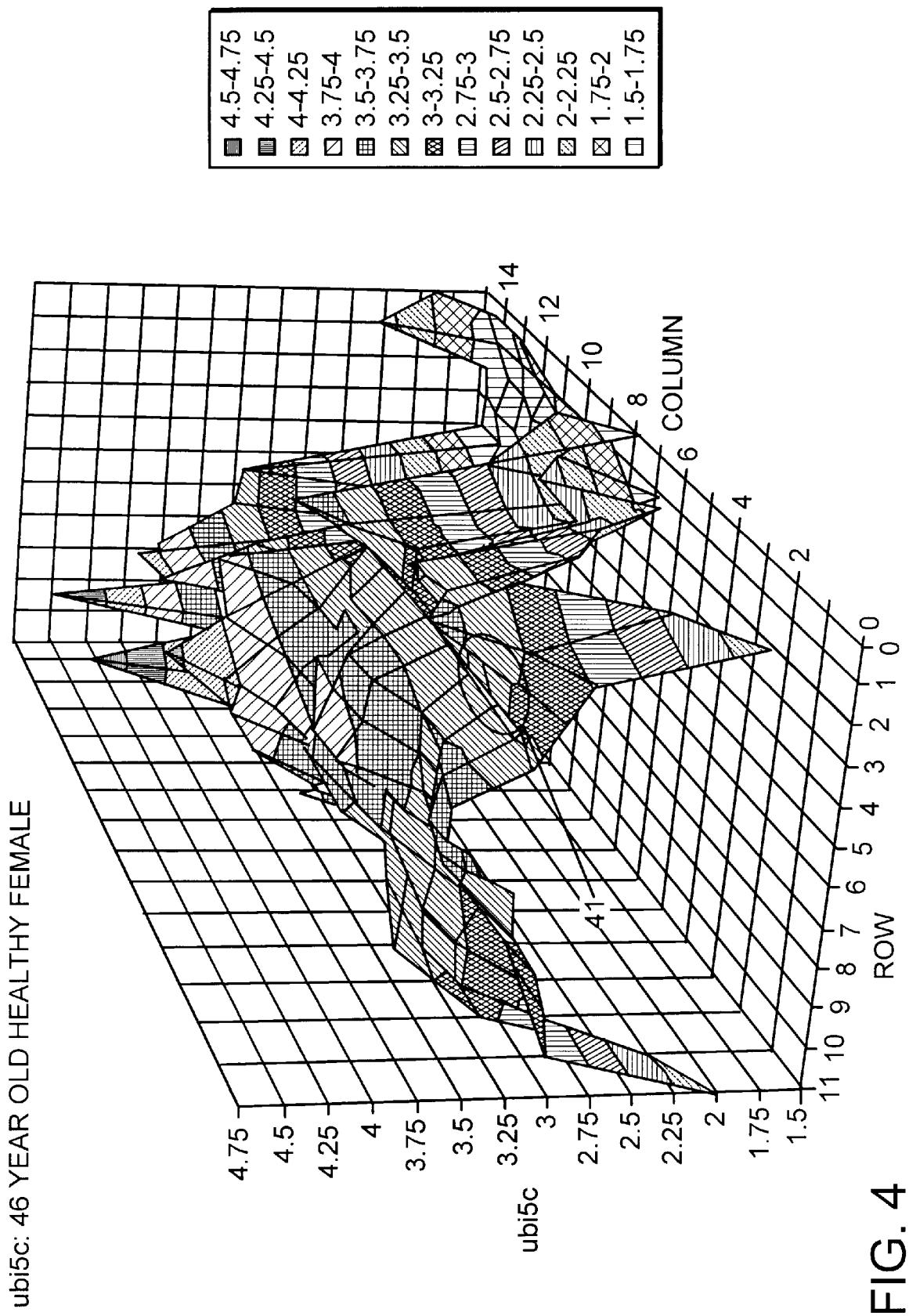

FIGS. 3 and 4 are three-dimensional surface plots of UBI-4b and UBI-5c respectively over a two-dimensional region of the calcaneus of a 46-year old healthy female. In these plots and in the plots following through FIG. 8, the axis marked "Column" on the right approximates the heel-to-toe axis, with the heelmost position (i.e., toward the back of the heel) lying at the origin. (On this and subsequent plots, the region presented may not necessarily include the near edge of the calcaneus.) The axis marked "Row" is in a direction perpendicular to the "Column" axis, again with the heelmost position (i.e., toward the bottom surface of the heel) at the origin. These two axes are used identify coordinates associated with the transducer pair $T_T$ and $T_R$ of FIGS. 1 and 2. The transducer pair may be in a fixed disposition relative to each other, as in cradle 166 of FIG. 16 of the Prior Application, so that an ultrasound pulse is transmitted from transducer $T_T$ along a path through the calcaneus to transducer $T_R$ and processed in the manner as described in the Prior Application. The pertinent UBI is determined with the two transducers in a given location. The transducers are then moved relative to the bone to a series of different locations so as to permit the determination of a collection of UBI values over an entire region of interest. (However, the particular manner in which the transducers are mounted and moved is not a part of the present invention.) The two axes (Column and Row) therefore identify the position of the transducer pair relative to the subject's foot. Finally, the vertical axis shows the pertinent UBI value determined for each location.

Although there are some differences between these two plots, they share remarkable similarities. Each plot exhibits a relatively broad plateau. The right-hand edge of the plateau —running generally along the heel-to-toe ("Column") axis—exhibits a cliff-like drop that is attributable to the edge of the calcaneus. In other words, the plots permit identification of the edge of the bone being assessed.

Furthermore, in each of FIGS. 3 and 4, the plateau itself exhibits some regularity; particularly in the realm of Column values of say, 1 through 6, the UBI value changes relatively little for Row values ranging from 3 to 8. This region, which in this description and the following claims is termed the "candidate region," has the characteristics that (i) it is set in from the edge of the bone and (ii) the UBI values over the region are relatively insensitive to the height above the heel-to-toe axis, i.e. to changes in the row value. In the candidate region. However, can be found a local trough, wherein the UBI values are at a local minimum. In FIG. 3, the local trough in the candidate region is identified as location 31, and in FIG. 4, the local trough in the candidate region is identified as location 41.

A position having a local minimum slope magnitude associated with a local trough (if a trough exists), in the candidate region, is referred to in this description and the following claims as the "reference location." The reference location is believed to result from anatomical properties of the calcaneus, and, as discussed below, is also believed to be useful in identifying a location that is particularly significant for UBI measurement. The reference location may also be identified using somewhat difference criteria. For example, we have found it desirable to favor a trough that is located relatively close to the origin, i.e. near the back and bottom of the calcaneus, but nevertheless set back from the edge thereof. This general area may be viewed as the candidate region, and the reference location identified as the trough (if present; otherwise the position of local minimum slope magnitude) in that region.

Figure 5:
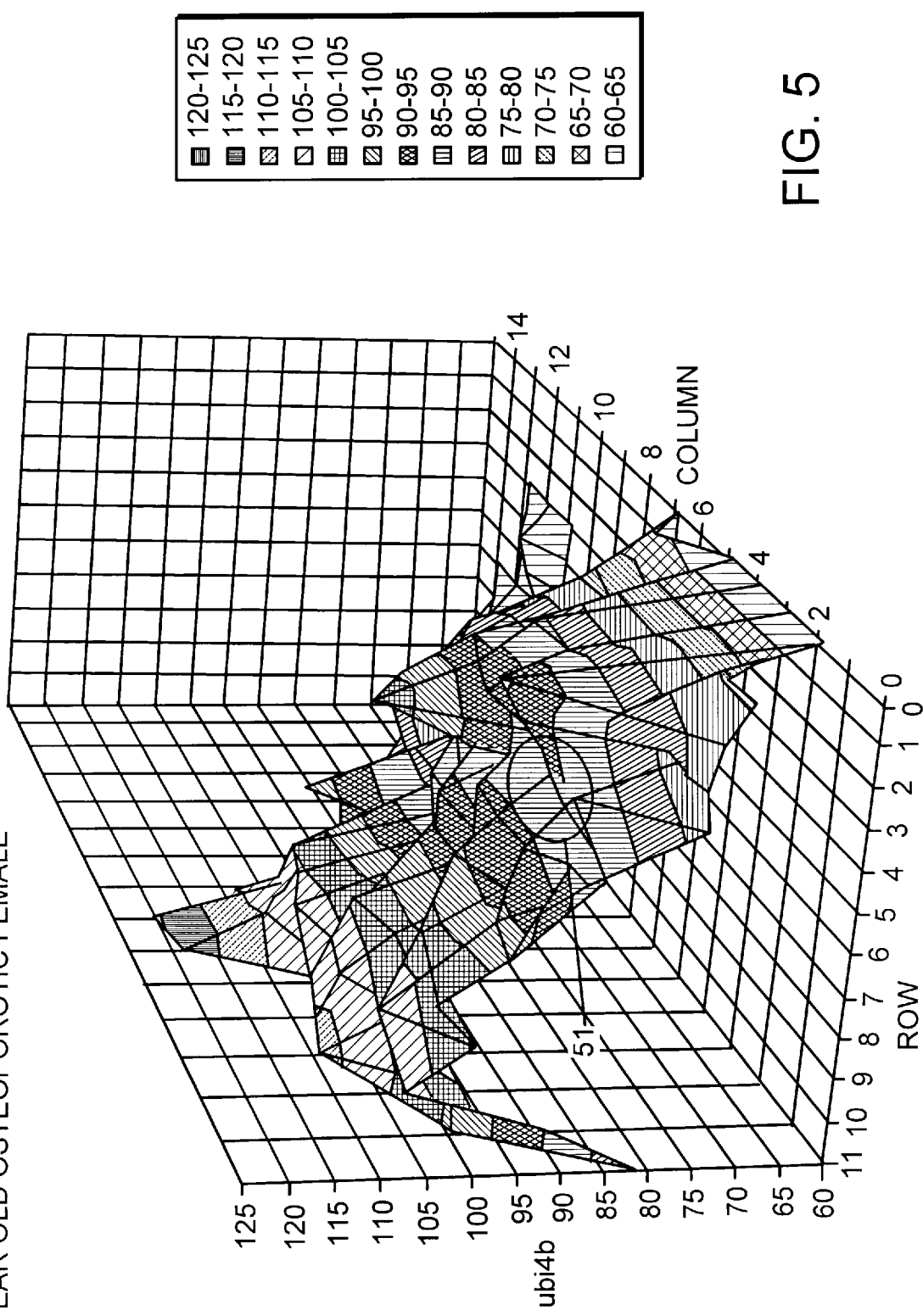
FIGS. 5 and 6 are surface plots of UBI-4b and UBI-5c respectively over a two-dimensional region of the calcaneus of a 45-year old osteoporotic female.
Figure 6:
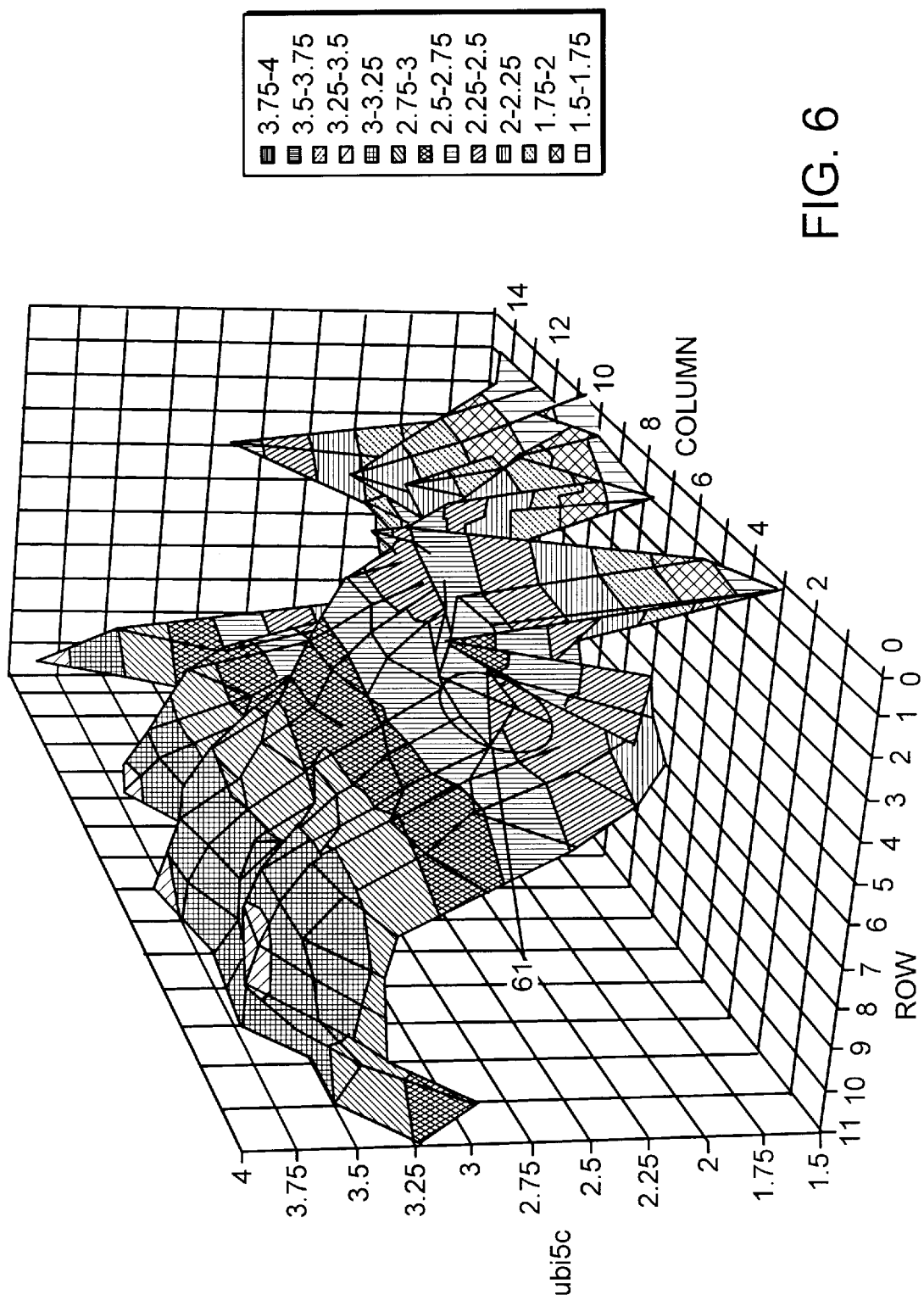

In contrast to FIGS. 3 and 4, FIGS. 5 and 6 are surface plots of UBI-4b and UBI-5c respectively over a two-dimensional region of the calcaneus of a 45-year old osteoporotic female. In these figures, the high and broad plateau in FIGS. 3 and 4 has been replaced a plateau that is relatively lower: the plateau of FIG. 5 is lower than that of FIG. 3, that of FIG. 6 is relatively lower than that of FIG. 4. This is most clearly evident if one looks in the candidate region: having column values between 1 and 6 and row values between 3 and 8. Moreover, in the candidate region one can identify the reference locations 51 and 61, where local troughs in the UBI values are present. The UBI value at reference location 51 is manifestly lower than that at reference location 31; it is also lower at reference location 61 than it is at reference location 41.

Figure 7:
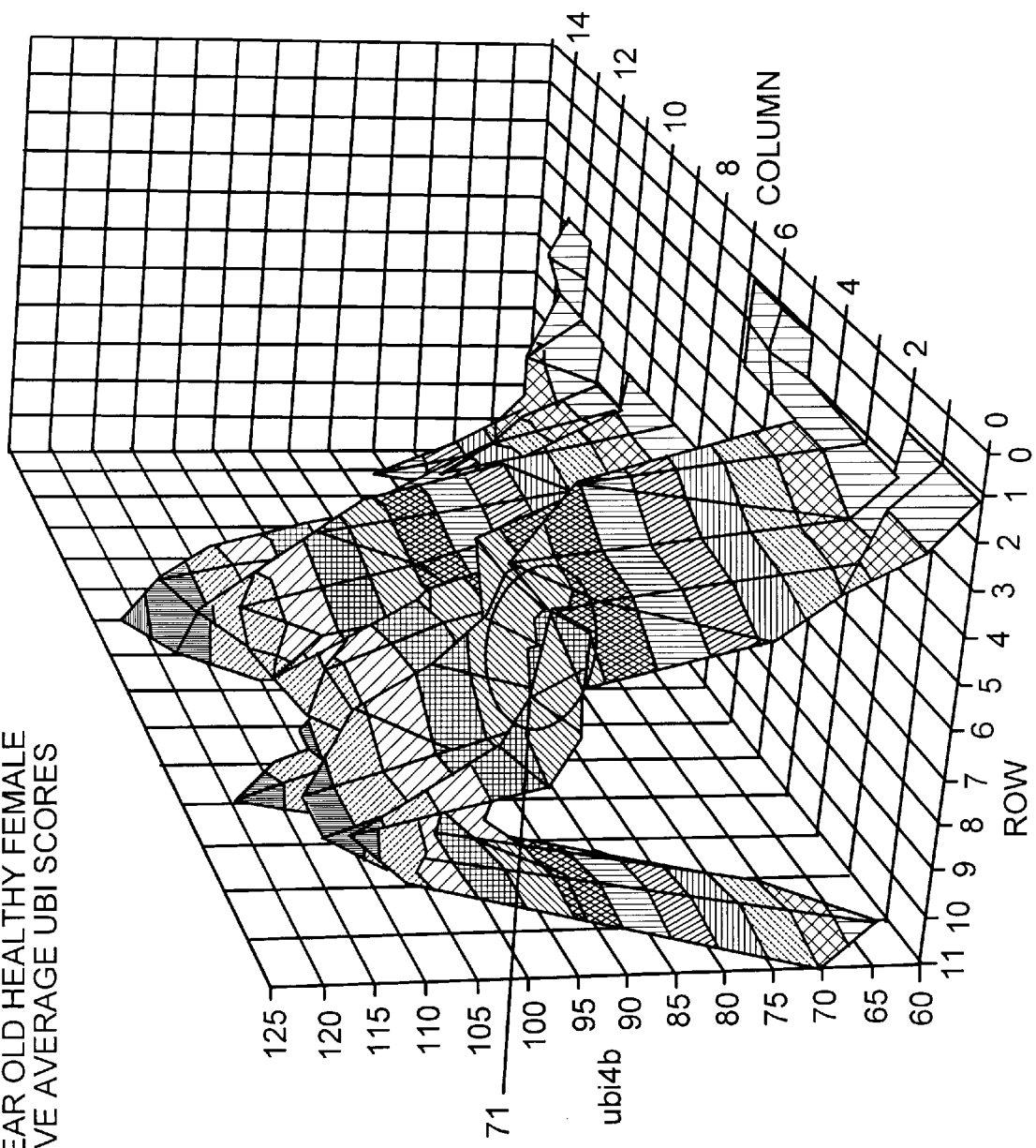
FIGS. 7 and 8 are surface plots of UBI-4b and UBI-5c respectively over a two-dimensional region of the calcaneus of a 76-year old female with a bone quality superior to that typical for her age.
Figure 8:
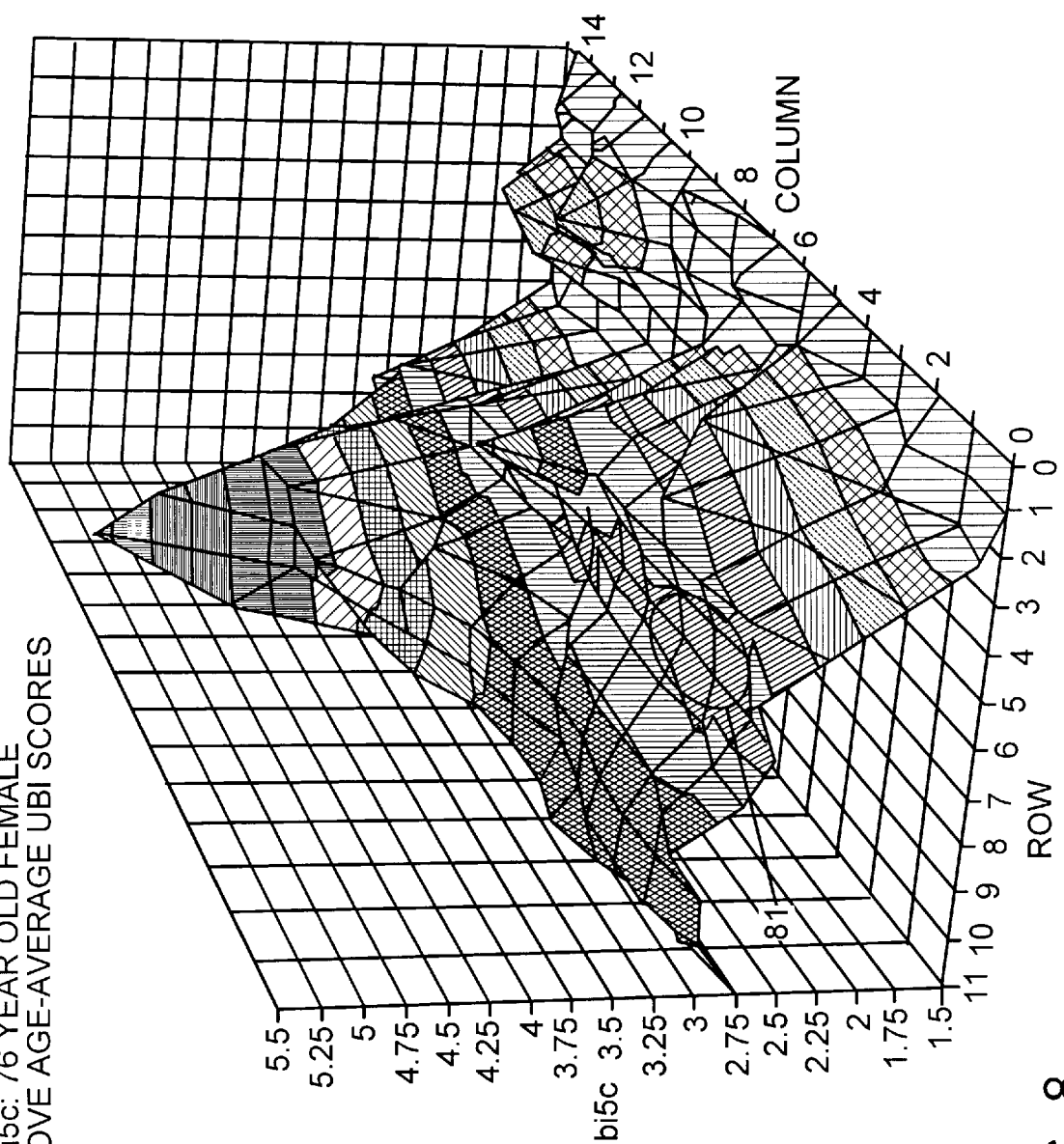
Figure 9:
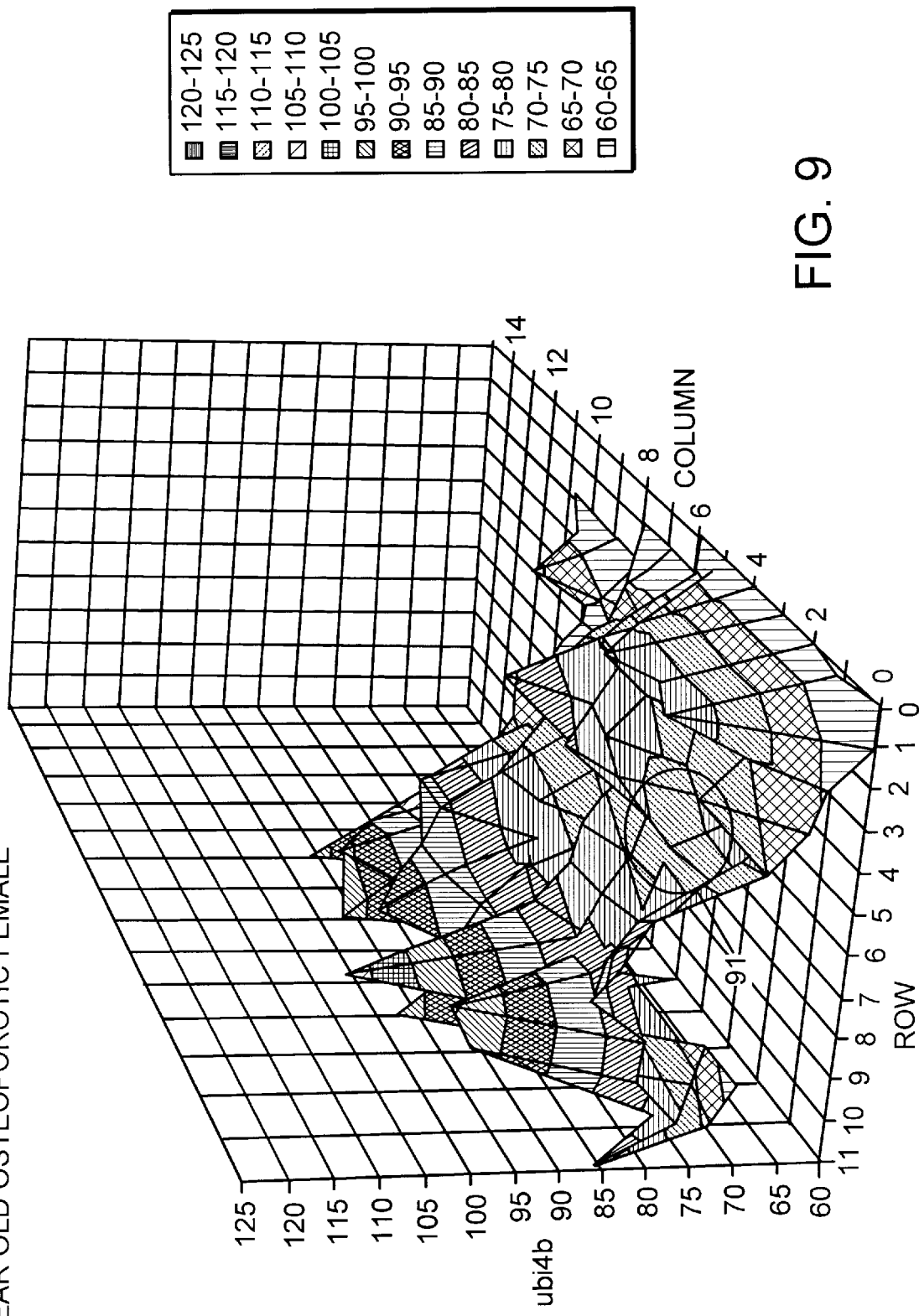
FIGS. 9 and 10 are surface plots of UBI-4b and UBI-5c respectively over a two-dimensional region of the calcaneus of an 83-year old female with osteoporosis.
Figure 10:
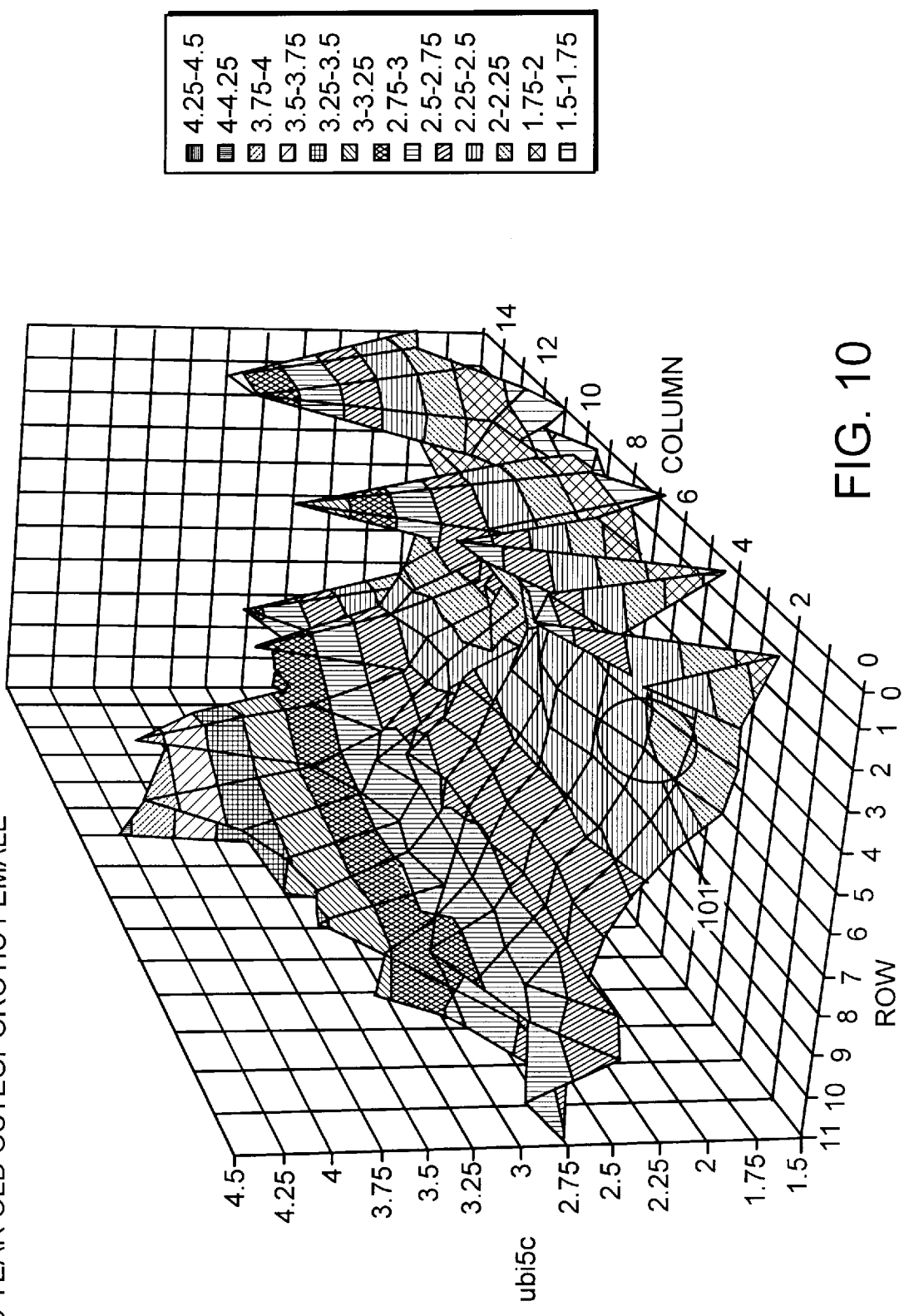
Figure 11:
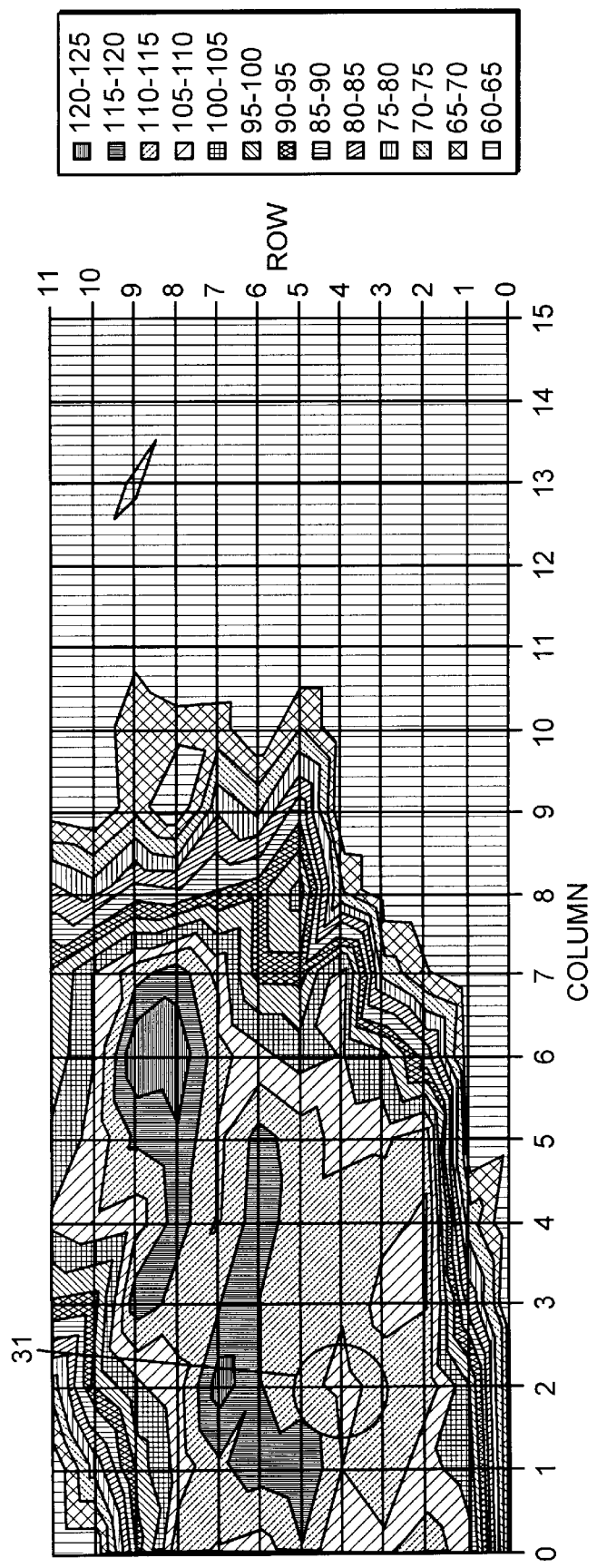
FIGS. 11–18 are topographical plots corresponding to FIGS. 3–10 respectively.
Figure 12:
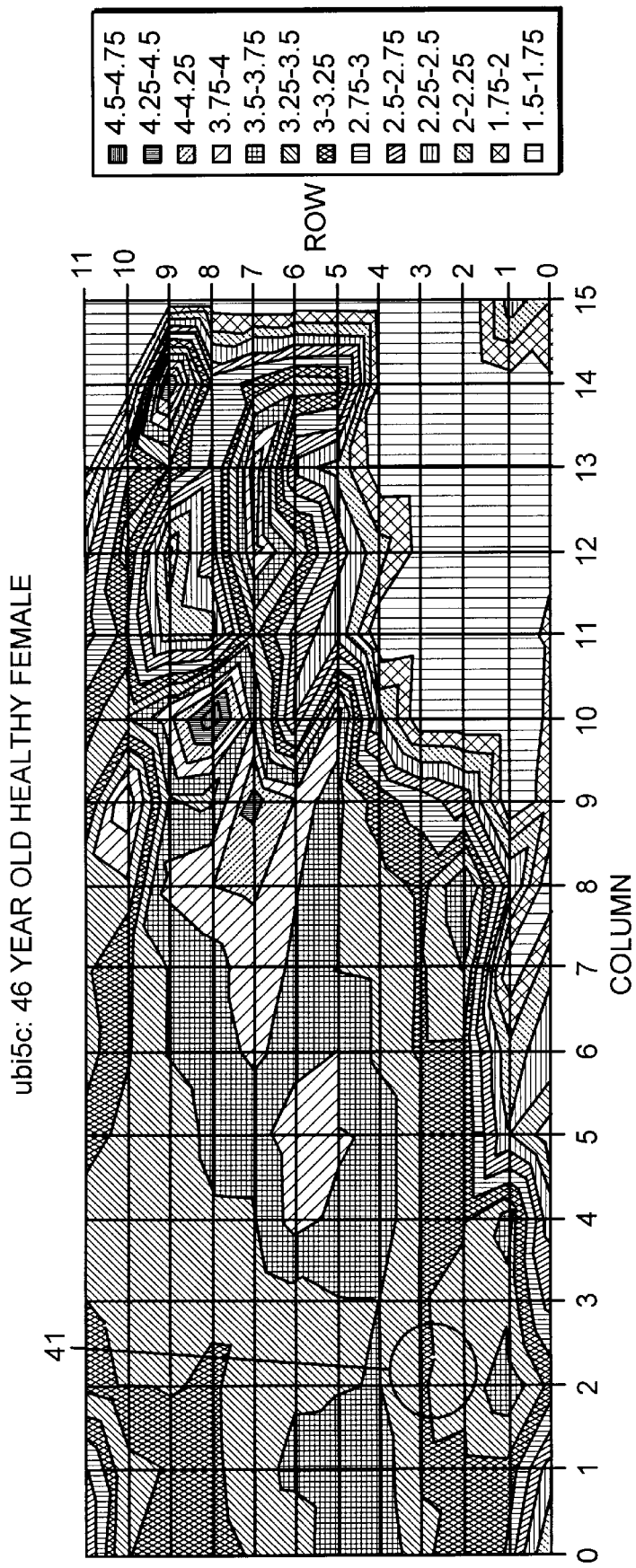
Figure 13:
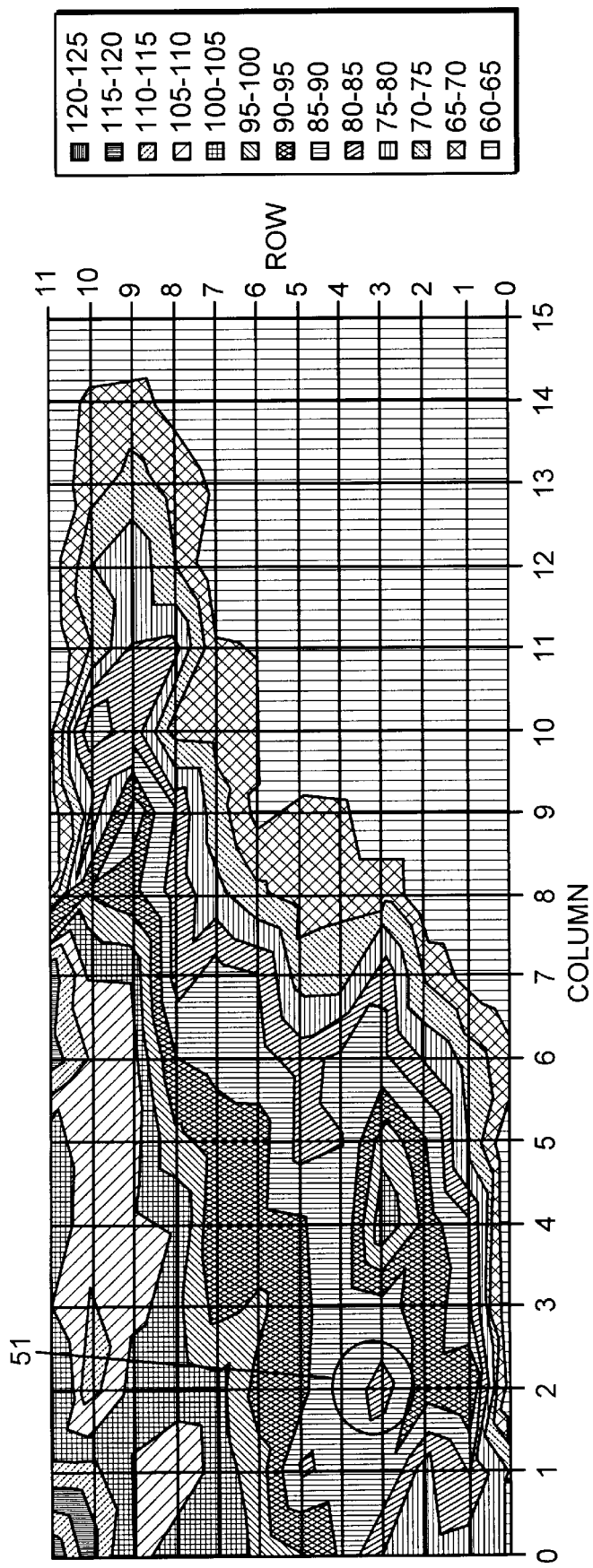
Figure 14:
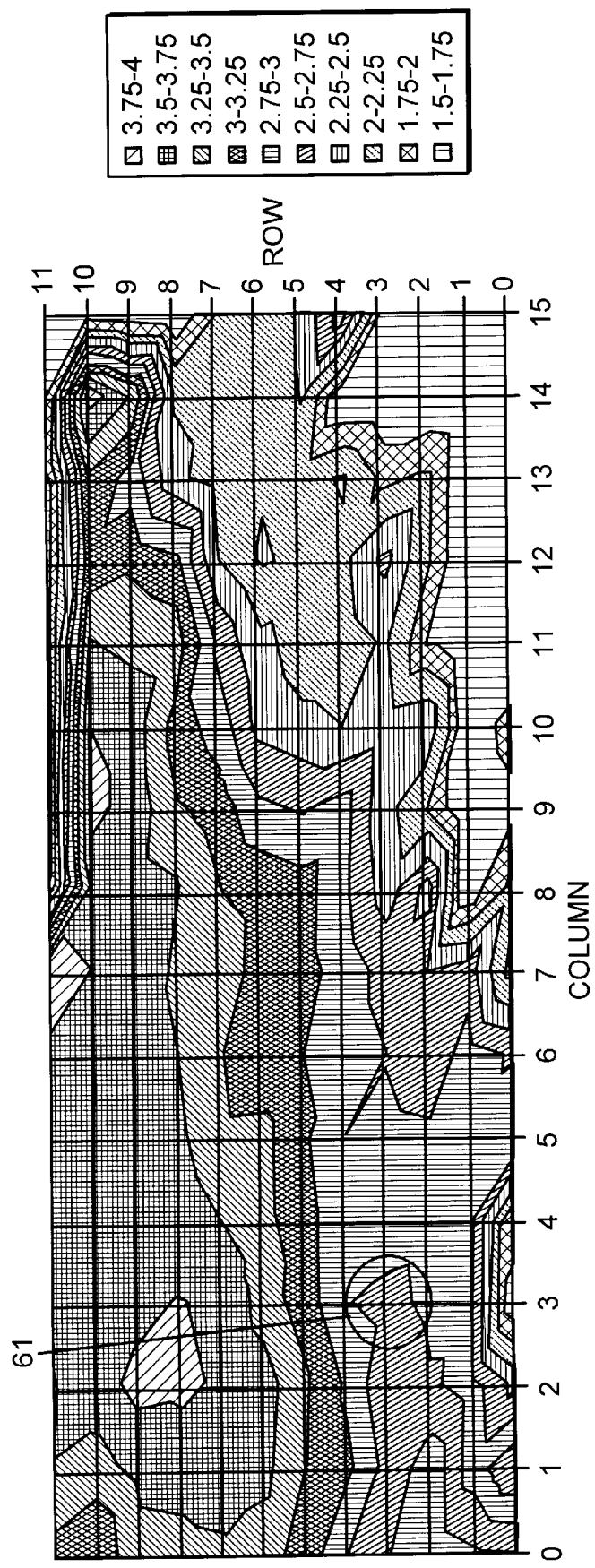
Figure 15:
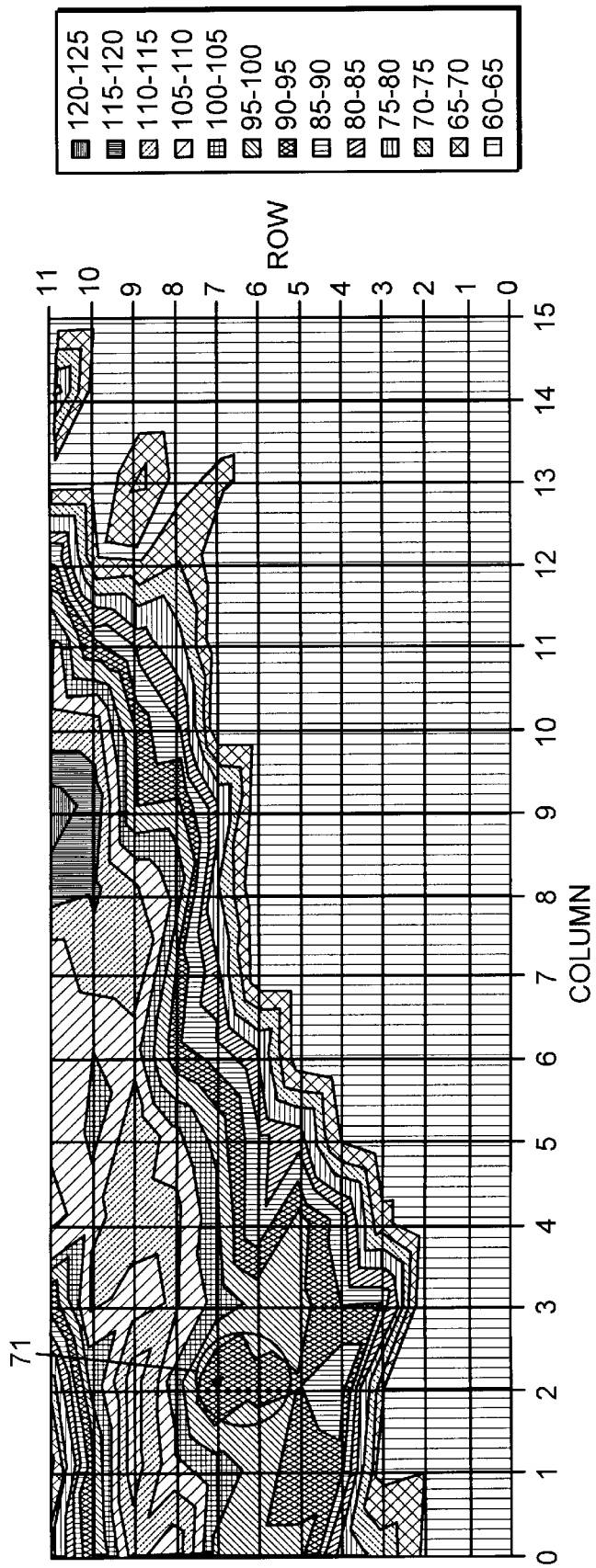

FIGS. 7 and 9 are surface plots of UBI-4b over a two-dimensional region of the calcaneus respectively of a 76-year old female with above age-average bone quality and of an 83-year old female with osteoporosis. In FIG. 7, it can be seen that the lowest portion of the bone edge is located approximately 3 rows above the heel-to-toe axis; the candidate region has column values between 1 and 3 and row values between 4 and 8. The local trough 71 identifies the reference location in the candidate region. In FIG. 9, the candidate region has column values between 1 and 3 and row values between 3 and 8. The local trough 91 identifies the reference location in the candidate region. Again, it can be seen that the UBI value at reference location 91 is manifestly lower than that at reference location 71. FIGS. 8 and 10 are surface plots of UBI-5c over a two-dimensional region of the calcancus respectively of the same two subjects as in the case of FIGS. 7 and 9, with the reference locations identified as items 81 and 101 respectively; similar results are shown in these plots to those in the case of FIGS. 7 and 9.

Use of the surface plots of FIGS. 3–10 has the disadvantage that the precise position coordinates of the reference location may in some cases be difficult to visualize, owing to the use of the 3D format. This difficulty may be resolved by recourse to topographical plots such as shown in FIGS. 11–18, which correspond to FIGS. 3–10 respectively. In FIGS. 11–18, the magnitude of the UBI is shown by shading rather than by a third coordinate value, so that locations by row and column are unambiguous. The reference locations previously discussed in connection with FIGS. 3–10 are marked in FIGS. 11–18.

From the foregoing examples, it can be seen that in accordance with an embodiment of the invention, the candidate region in general and the reference location in particular can be used to provide a UBI value for purposes of comparison among subjects as a measure of bone porosity and non-connectivity. Furthermore, the particular UBI that is used to identify the reference location or candidate region need not necessarily be the same UBI as is used to provide the final measure of bone porosity and non-connectivity. For example, one might use UBI-5c to identify the reference location and then use UBI-4b as the measure of bone porosity and non-connectivity at the reference location. Indeed, as discussed above and in the Prior Application, the UBI can be one other than any of those specifically numbered and described. For example, the manifest differences in graphs of the type above between relatively porous, non-connective bone on the one hand and healthy bone on the other hand suggest another UBI that is a measure of the volume beneath the candidate region or the volume beneath a defined area that surrounds the reference location. Also described below, it is possible in certain cases to derive an estimate of BUA from a UBI.

Up to this point in the description, the UBI surface itself—the collection of UBI values that have been obtained over a region—has been examined and used to identify a location where a UBI value will be utilized as the measure of bone porosity and non-connectivity. (The location with respect to which a UBI value will be utilized as the measure of bone porosity and non-connectivity is termed the "target location" for purposes of this description and the following claims.) In other words, the target location may, but need not necessarily, be the reference location. It is therefore within the scope of the present invention, as one embodiment thereof, to identify the target location by geometric means external to the subject's body part. Alternatively, the target location may be defined in terms of the edges of the bone, as determined by the device itself. (The location selected in this manner is termed the "default location" for purposes of this description and the following claims.) Thus, for example, the default location may be determined in reference to the bottom and back of the heel bone and may involve scaling of default dimensions based on other parameters including, but not limited to, the size of the foot of the subject. This enables the device to place the target region in an anatomically analogous location on every subject's bone regardless of the offset of that bone caused by varying amounts of soft tissue. After the default location has been ascertained, the transducers pair $T_T$ and $T_R$ in a fixed relative disposition, such as the cradle 166 of FIG. 16 of the Prior Application, may be moved to the default location, and then the appropriate UBI may be determined at the default location. In other words, the default location may be described, for example, as absolute distances in the coordinate system (x-location and y-location) described above for the graphs of FIGS. 2 through 8: for example, 1 cm forward (along the x axis) and 2 cm up (along the y axis)—if these were the coordinates ascertained for the class of subjects in relation to a bone-fixed coordinate system.

The default location may be ascertained for a class of subjects by experimental determination of the reference location for each subject in the class; the median location can be used as the default location. While it is possible to use a single default location for all human subjects, it may be desirable in many instances to specify the default location as a function, for example, of gender and age range of the subject, and/or shoe size, external foot geometry, etc.

Once the default location has been ascertained, it is possible, in one embodiment of the invention, to use the default location as the target location for the UBI measurement. Alternatively, a specified region defined with respect to the target location may be processed to derive another measurement. For example, in accordance with a preferred embodiment of the invention, a window 8 mm high by 4 mm wide, following the contour of the bottom of the foot and located 4 mm for a line defined with respect to the edge of the bone may be averaged to provide a measure of bone porosity.

In another embodiment of the invention, however, the target location is determined as a function of both the default location and the reference location. The function may, for example, be a weighted average of the two locations. As a further example, the weights may be adjusted to favor the reference location when the UBI surface shows a sufficiently pronounced local trough in the candidate region and to favor the default location when the UBI surface fails to indicate a reference location with a desired level of confidence.

Figure 19:
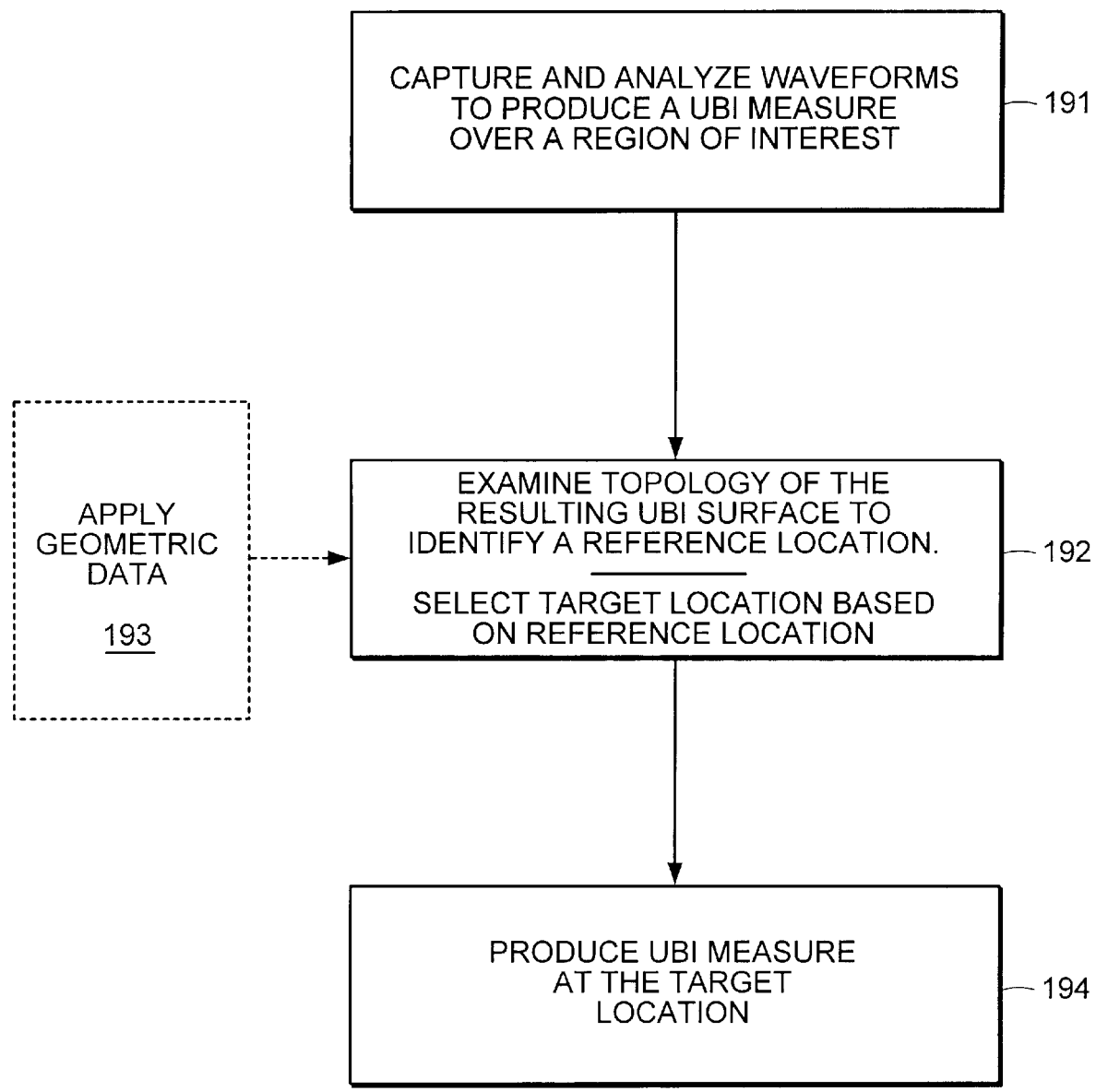
FIG. 19 is a logical How diagram of the process in accordance with a preferred embodiment of the invention for producing a UBI measure at a target location.

FIG. 19 is a logical flow diagram of the process in accordance with a preferred embodiment of the invention for producing a UBI measure at a target location. The process described herein utilizes procedures and characteristics described above in connection with FIGS. 3 through 18. In accordance with step 191, the transducers pair $T_T$ and $T_R$ in a fixed relative disposition such as the cradle 166 of FIG. 16 of the Prior Application, are utilized so that an ultrasound pulse is transmitted from transducer $T_T$ through the calcaneus to transducer $T_R$ and processed in the manner as described in the Prior Application. The waveforms received by transducer $T_R$ are thus captured and analyzed to produce a UBI measure in a given location. The transducers are moved relative to the bone to a series of different locations so as to permit the determination of a collection of UBI values over an entire region of interest.

In accordance with step 192, the topology of the resulting UBI surface is examined so as to identify a reference location. In this step, a target location is selected based on the reference location. The target location may in fact be the same as the reference location or, as a further embodiment, geometric data may be applied in step 193, so that the target location is a function of both geometric data and the reference location. Finally, in step 194, there is produced an appropriate UBI measure at the target location.

Figure 20:
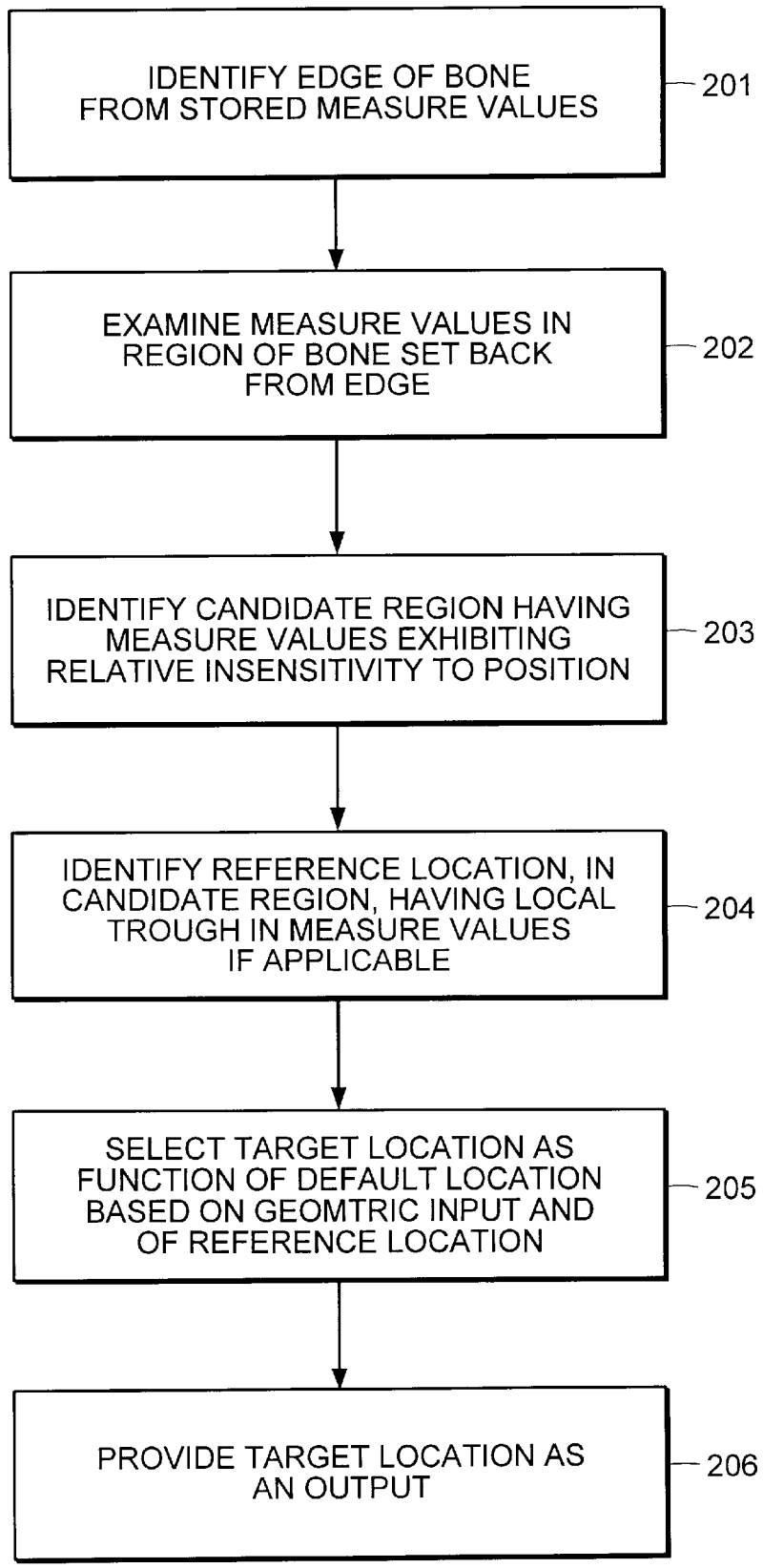
FIG. 20 is a logical flow diagram of the process in accordance with the embodiment of FIG. 19 for identifying a reference location.

FIG. 20 is a more detailed logical flow diagram of the process in accordance with steps 192 and 193 in the embodiment of FIG. 9 for identifying a target location. In step 201, the stored measure values are analyzed to identify the edge of the bone. In step 202, after the bone edge has been identified, the UBI measure values in the region of the bone that is set back from the edge are examined. As a result of the examination in step 203, there is identified a candidate region having measure values that exhibit relative insensitivity to position. Next, in step 204, there is identified a reference location (if present) in the candidate region, that has a local trough in measure values; if no local trough is present, then the location to be identified has a local minimum slope magnitude. In step 205, there is selected a target location as a function of both a default location based on geometric input data and on the reference location. Finally, in step 206, the target location is provided as an output.

Figure 21:
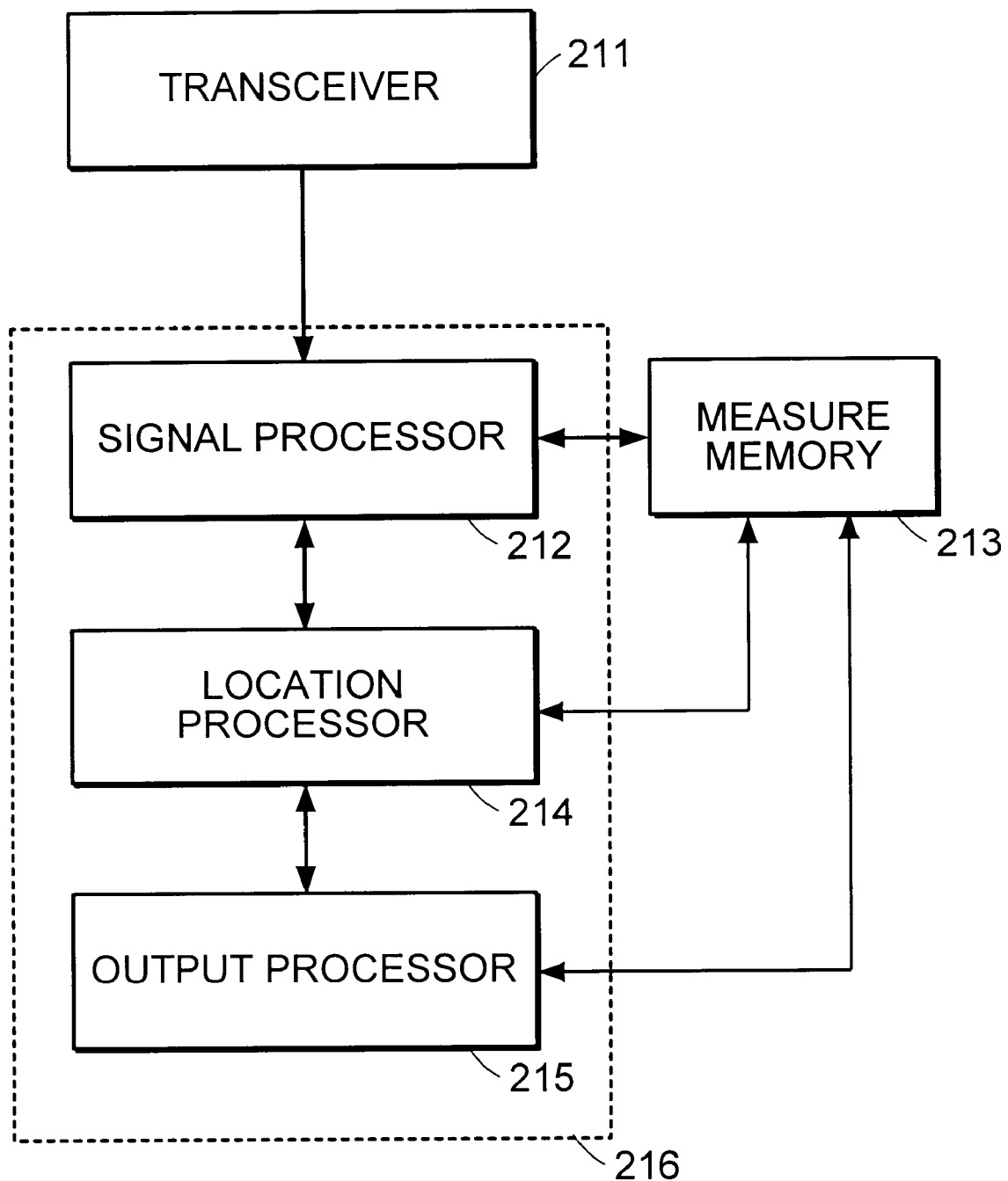
FIG. 21 is block diagram of an apparatus in accordance with a preferred embodiment of the present invention for implementing the processes of FIGS. 19 and 20.

These processes can be performed in an apparatus configured as shown in FIG. 21, which is a block diagram of an apparatus in accordance with a preferred embodiment of the present invention for implementing the processes of FIGS. 19 and 20. An acoustic transceiver 211 has a signal generator for producing, when coupled to a transducer, an acoustic pulse, having energy distributed over a frequency range. The transceiver 211 also has a transducer assembly, which transducer assembly includes a plurality of transducers and provides a pair of transducers in spaced relationship with respect to the bone. A first one of the pair of transducers is coupled to the signal generator so as to provide an acoustic pulse and a second one of the pair receives an acoustic signal resulting from propagation of the acoustic pulse along a path that includes the bone. The transducer assembly is configured so that the path may be disposed in a plurality of positions so as to pass through a plurality of locations within a selected region of the bone.

A signal processor 212 is in communication with the second one of the pair of transducers. The signal processor 212 provides a UBI value, associated with each of the locations, that is indicative of at least one of spectral or temporal components of a portion, up to the whole amount thereof, of the signal received by the second one of the pair of transducers. The signal processor 212 operates in communication with a value memory 213 for storing the UBI values associated with the locations.

It is to be noted that the operation of the signal processor on data referring to distinct locations is described herein, for heuristic purposes, in terms of a value memory for storing values for subsequent manipulation. As known to persons skilled in the art of data processing, real-time strategies may equally be applied for manipulating spatial data, such as, for example and without limitation, adaptive gradient searches. "Value memory," as used in this description and in the appended claims, is thus used in the sense of an array of values, not necessarily concurrently extant in time. It is additionally to be noted that the correspondence between stored or manipulated values and physical locations may not be one-to-one or unique, and that averaging of data from discrete locations prior to further processing is encompassed by the claims of the present invention.

A location processor 214 selects a target location based at least in part on the values stored in the value memory, and an output processor 215 provides as an output a quantity associated with the target location. In practice the signal processor 212, the location processor 214, and the output processor 215 may, but need not necessarily, be realized as a single microprocessor (such as the microprocessor 21 of FIG. 2) implementing processes that have been programmed in software to provide the separate functions of each processor.

In addition, or alternatively to, the use of mapping for the selection of regions of diagnostic utility, figures of merit derived from the intrinsic shape or topology of the spatial maps may also be used for diagnostic purposes. For example, the average slope in the vicinity of the local troughs may provide important additional information. The use of topological measures is best appreciated with reference to FIGS. 27–30, which present cross sectional views of the surface plots of FIGS. 4, 6, 8, and 10. More particularly, FIGS. 27–30 present the UBI-5c data for the same four subjects as shown in FIGS. 4, 6, 8, and 10, as cross-sectional views looking into the surface plots of FIGS. 4, 6, 8, and 10 in a direction parallel to the heel-to-toe axis. Identical reference numerals in FIGS. 4, 6, 8, 10, and 27–30 refer to identical features.

Figure 28:
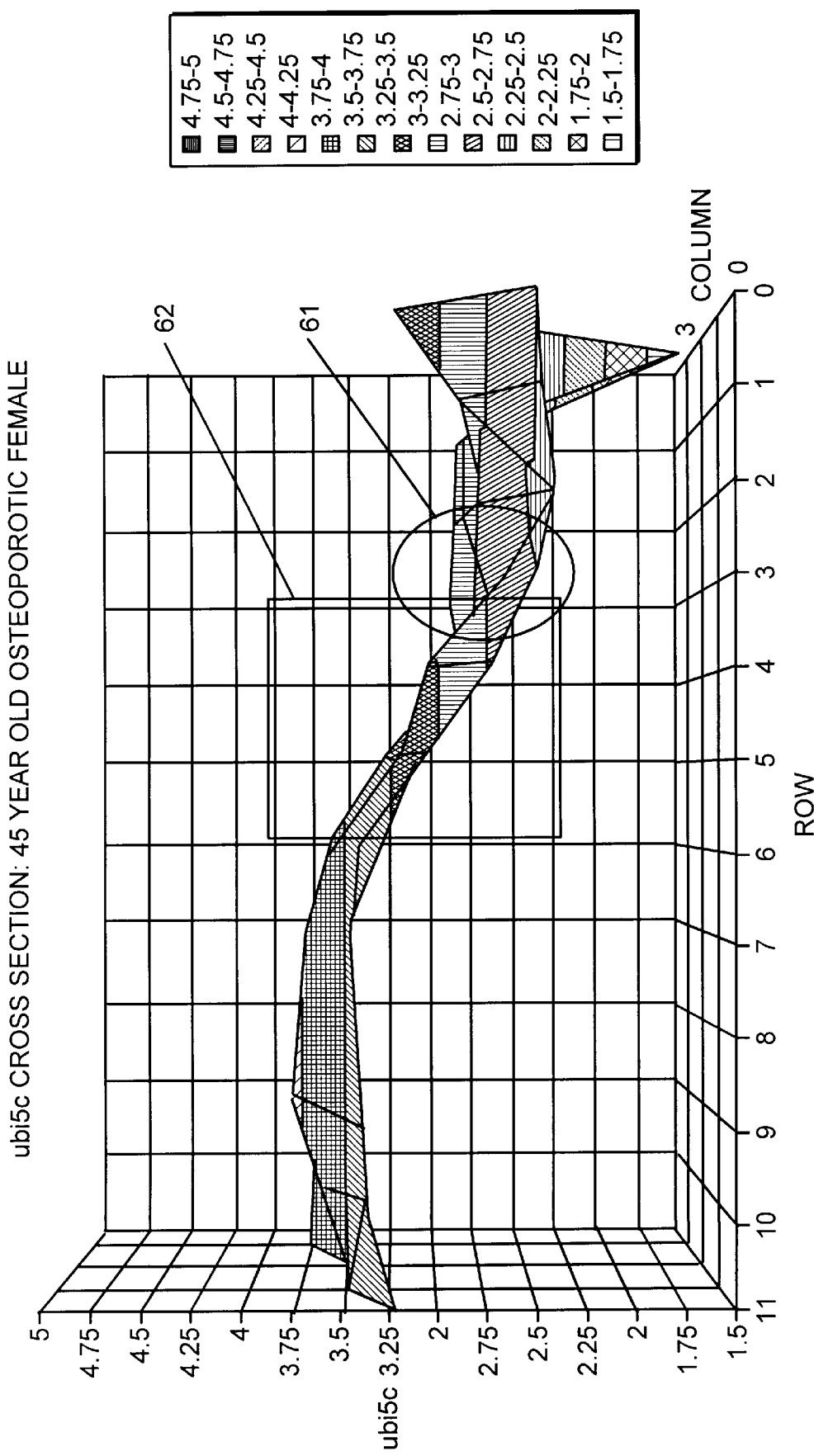
FIG. 28 is a cross-section of the surface plot of UBI-5c of FIG. 6 looking along an axis parallel to the heel-to-toe axis.
Figure 29:
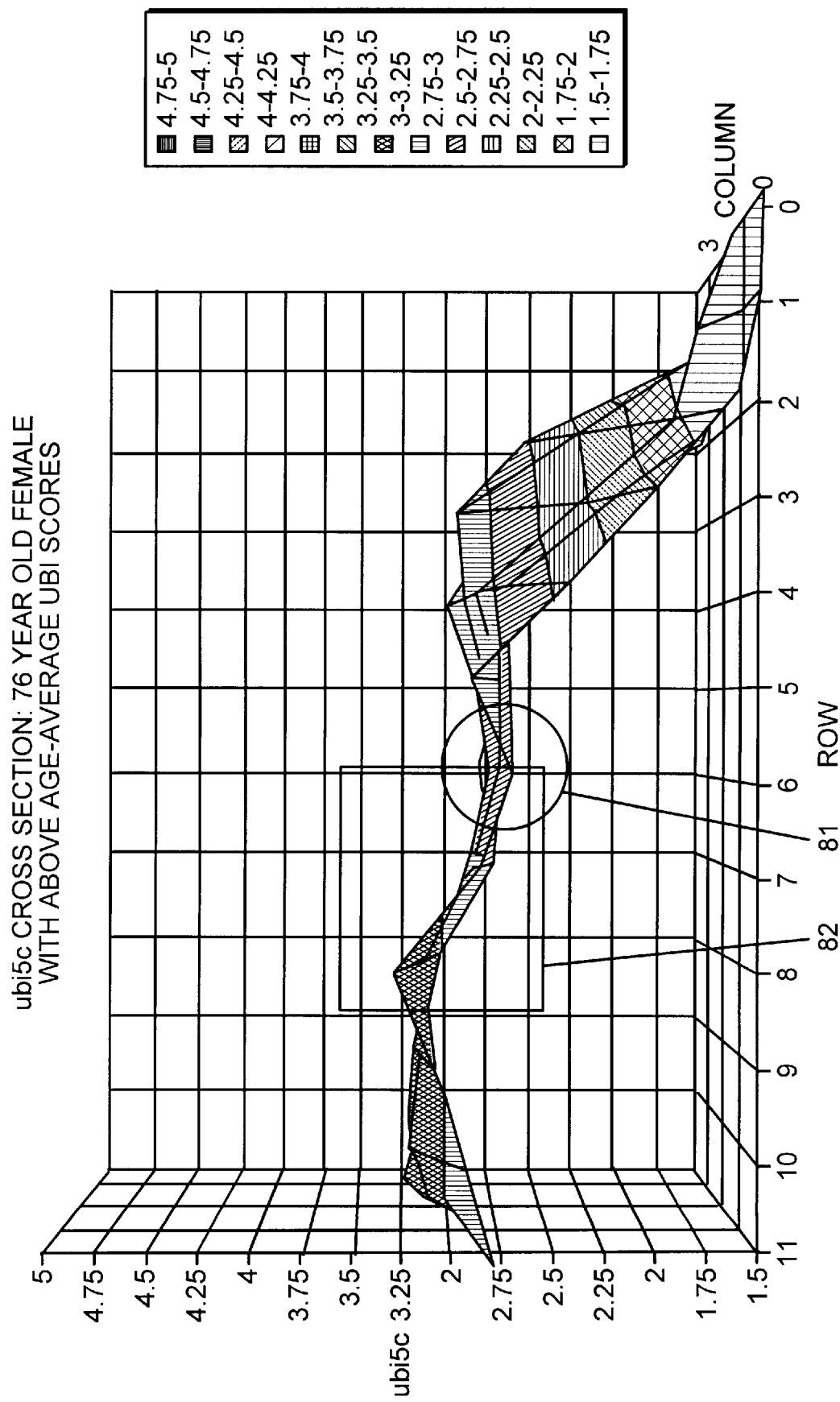
FIG. 29 is a cross-section of the surface plot of UBI-5c of FIG. 8 looking along an axis parallel to the heel-to-toe axis.

Comparison of FIGS. 28 and 29, plotting UBI-5c scores, respectively, for a 45-year-old osteoporotic female and 76-year-old female with above-average UBI scores, shows similar minimum values for UBI-5c, located at troughs 61 and 81. However, the average slopes on the selected regions designated 62 and 82, starting at troughs 61 and 81 and proceeding upward for about 3 rows (about 1 cm) are dramatically different. Since the subject for FIG. 28 is known to be osteoporotic and the subject for FIG. 29 is known to be healthy, the steeper slope may be associated with poorer condition of the bone. This result is opposite to that which would be obtained by simply averaging the UBI-5c score over the larger regions 62 and 82.

Figure 27:
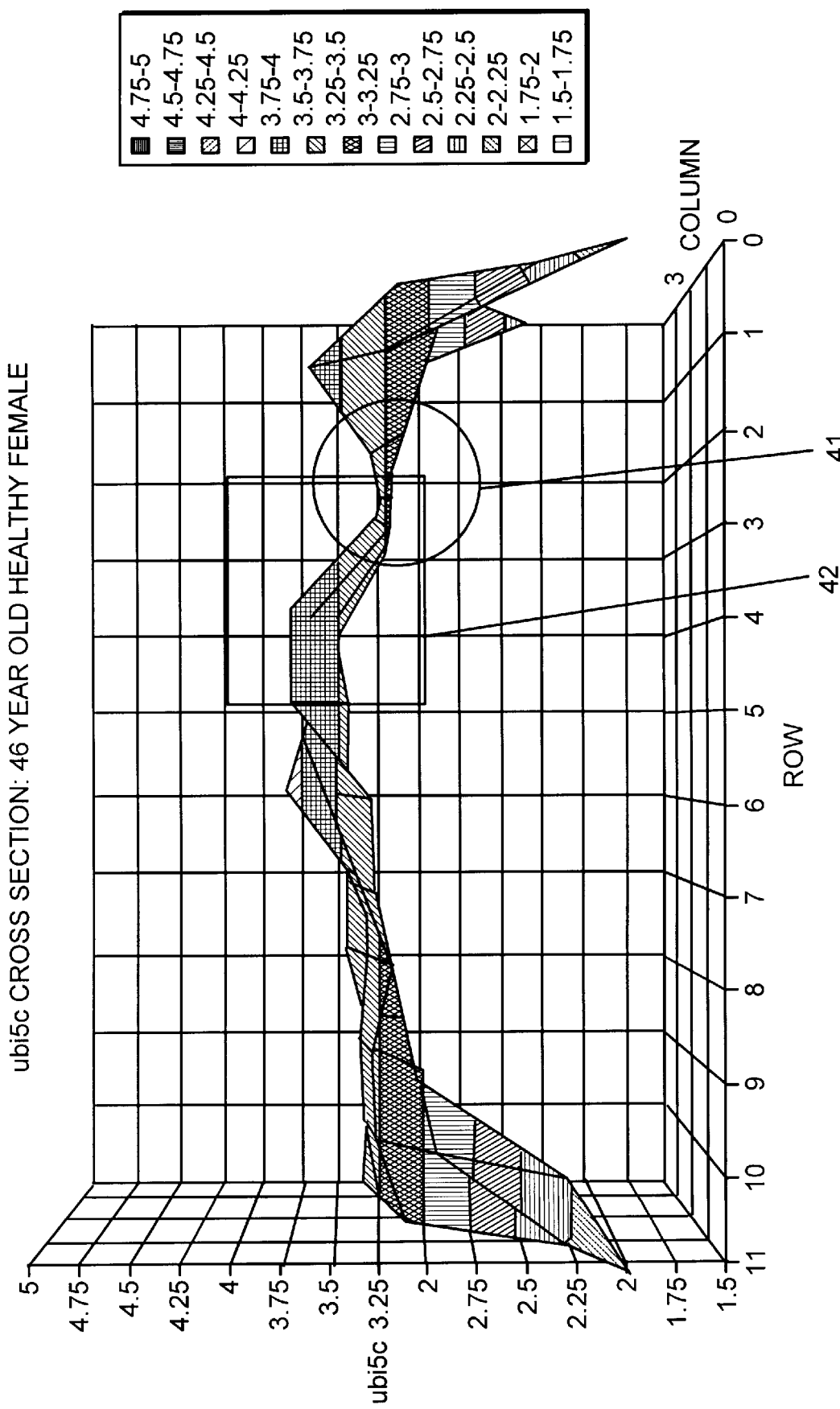
FIG. 27 is a cross-section of the surface plot of UBI-5c of FIG. 4 looking along an axis parallel to the heel-to-toe axis.
Figure 30:
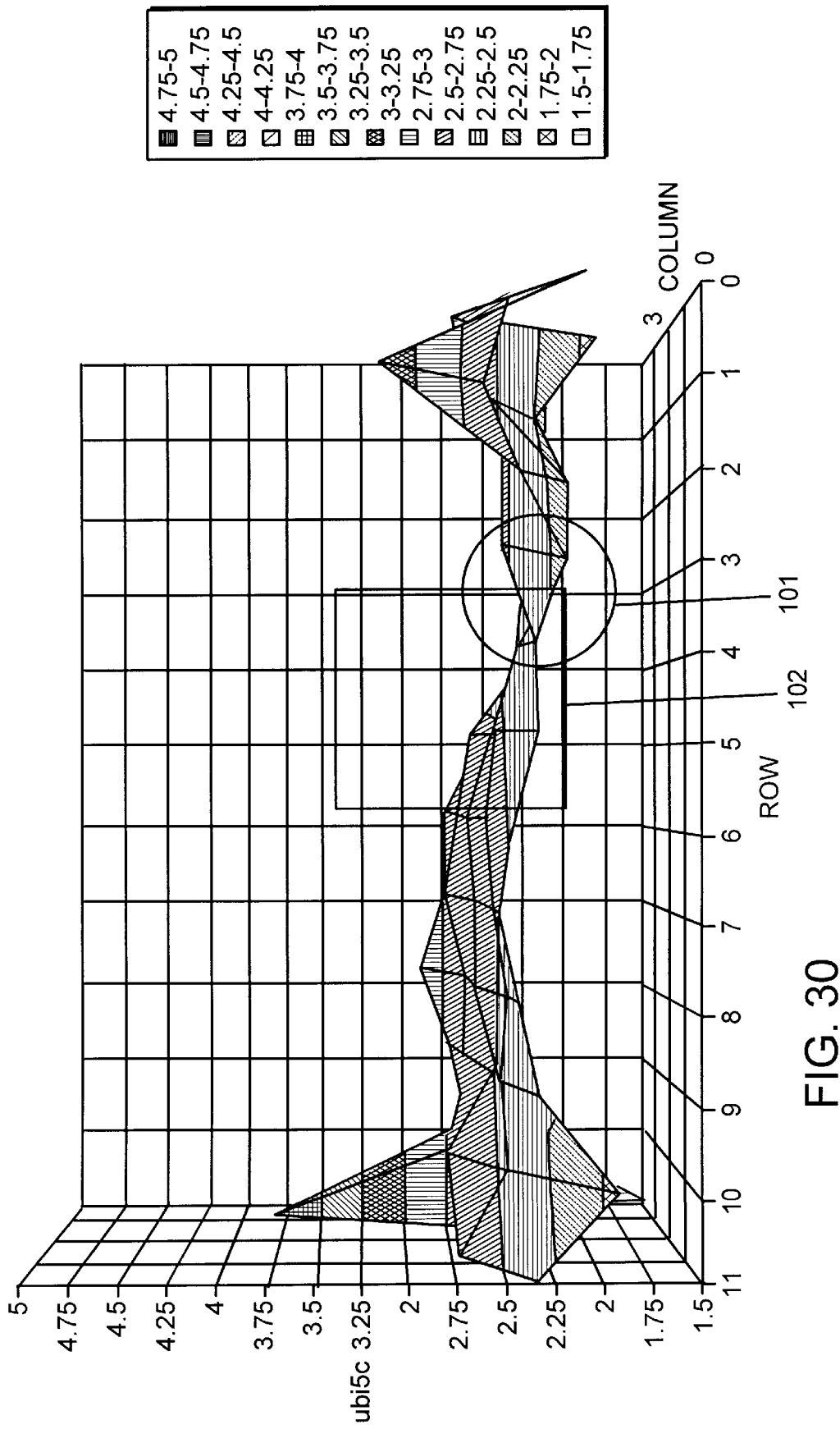
FIG. 30 is a cross-section of the surface plot of UBI-5c of FIG. 10 looking along an axis parallel to the heel-to-toe axis.

In a similar manner, FIGS. 27 and 30, plotting UBI-5c scores, respectively, for a 46-year-old healthy female and an 83-year-old osteoporotic female, show relatively shallow slope in selected regions 42 and 102 near respective local troughs 41 and 101 of the UBI-5c surface plots. Since the average slope is low for both the 46-year-old healthy subject and the 83-year-old osteoporotic subject, it is clear that the slope taken alone is not as effective an indicator of bone quality as the average slope taken in combination with the average UBI-5c value near the local trough. The combination of slope and UBI-5c value at the trough may enhance the diagnostic utility of the spatial maps. It is to be understood that other measures of UBI topology, such as, for example, the maximum gradient, may be used, and, furthermore, that similar techniques applied to other UBI measures, alone or in combination, are within the scope of the present invention.

Another application of the methods and apparatus described herein are for providing an earlier indication of the deterioration of bone quality than would be provided by the value alone of a bone quality measure at specified location. All of the foregoing techniques, alone or in combination, may be used to determine a propensity for a subject to change of porosity of bone, applying methods of longitudinal clinical study known to persons of ordinary skill in the art.

Figure 16:
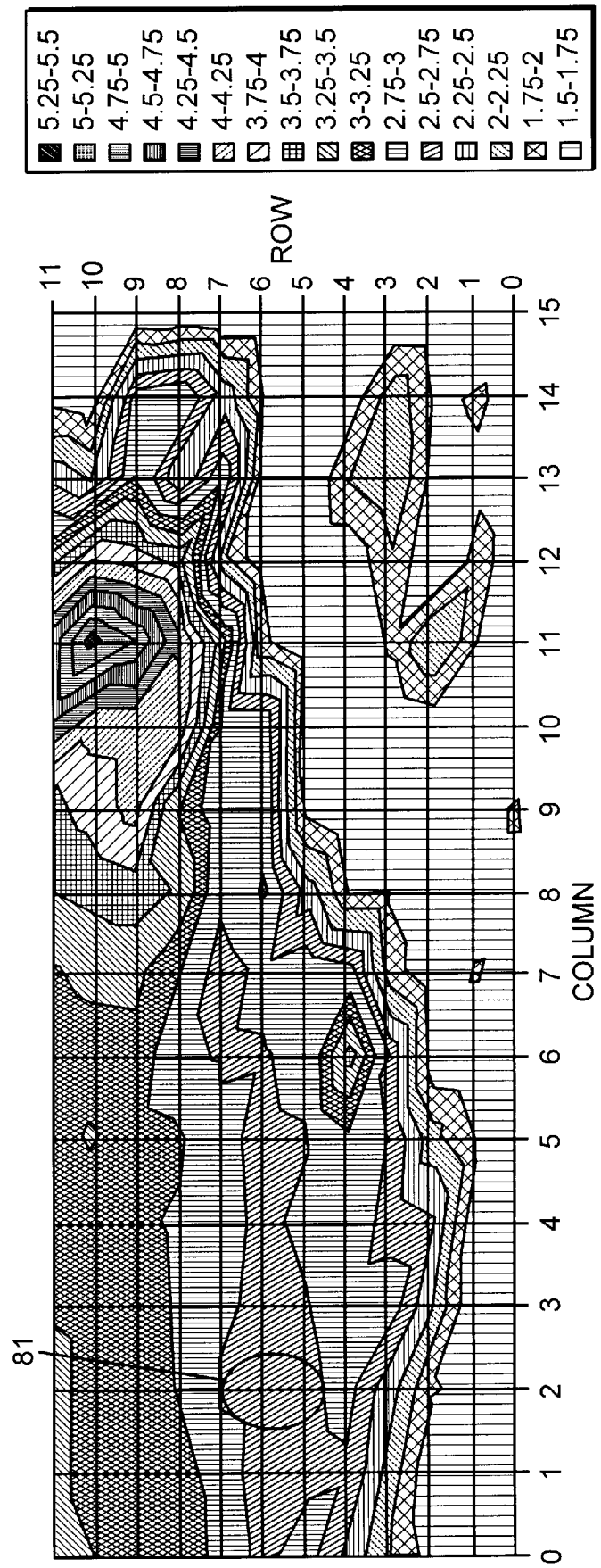
Figure 17:
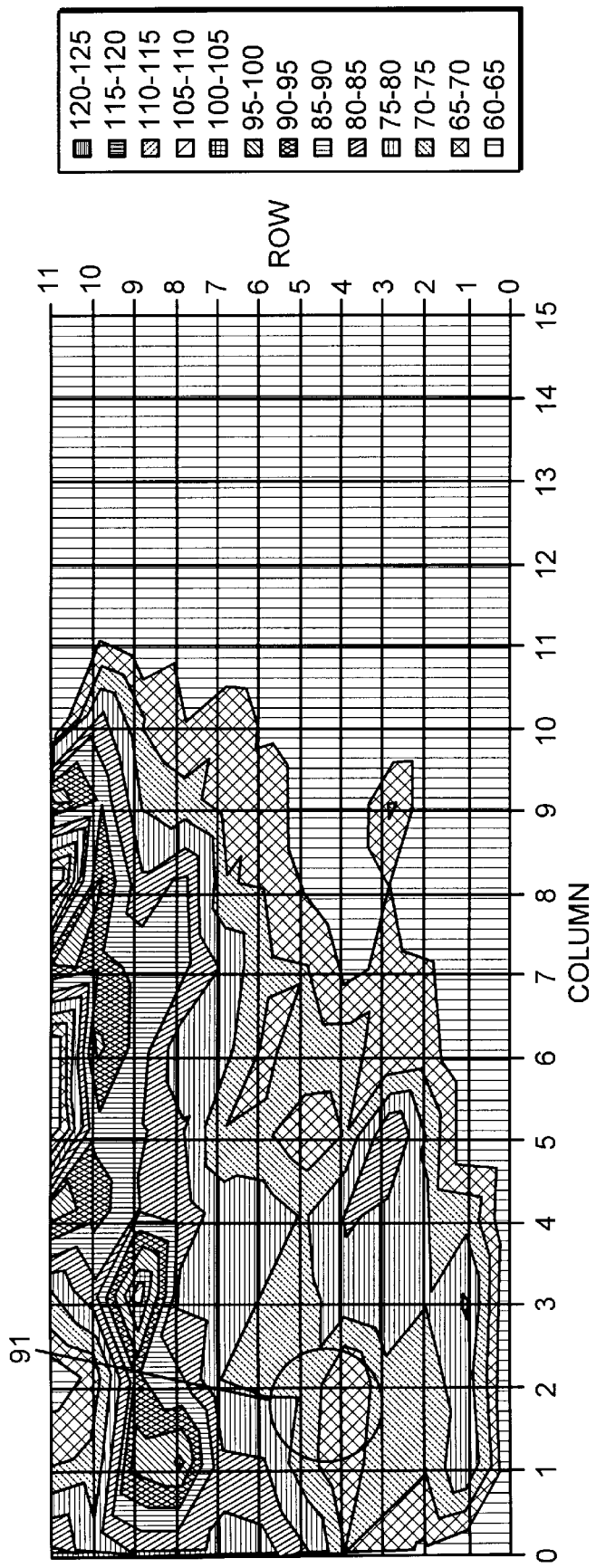
Figure 18:
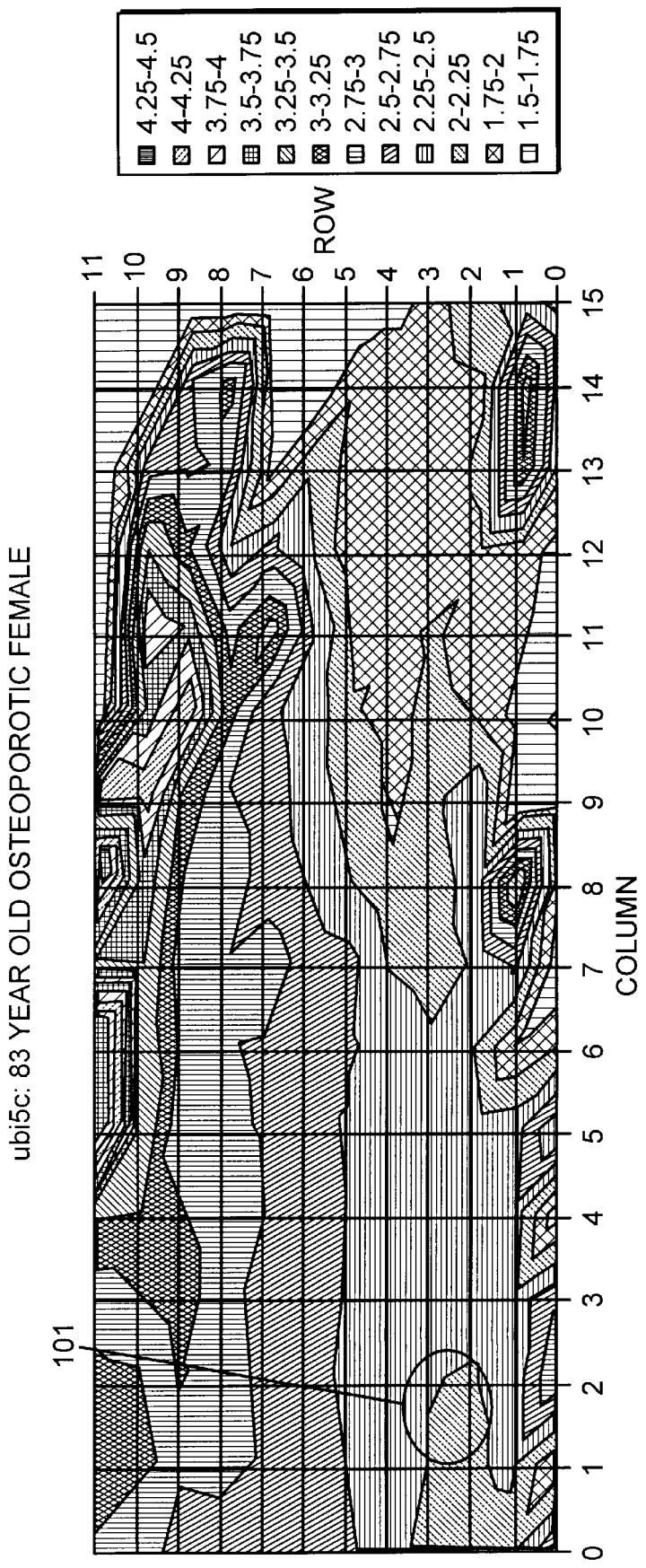

Although the transducer assembly, as previously described, may be implemented using the cradle 166 of FIG. 16 of the Prior Application, it is within the scope of the present invention to utilize a transducer assembly in which a plurality of transducers are disposed on one or more sides of the bone and the path through the bone is varied by electrical switching to determine the pair of transducers that is actually employed in each instance.

Figure 22:
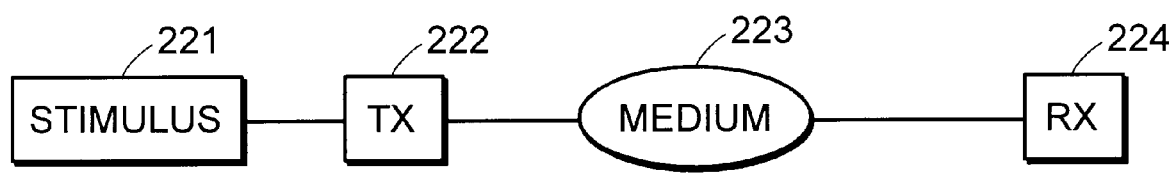
FIG. 22 is a schematic model of the ultrasonic analysis system for purposes of estimating other measures of bone integrity from one or more UBI measures in accordance with an embodiment of the present invention.

We next discuss an approach permitting the determination of an estimate of BUA from a UBI measure, such as UBI-5c. While the method described hereinafter provides an estimate of BUA, this estimate is intended to be of clinical utility to a user and there is no implication that the UBI measures are subject to the same limitations and inherent deficiencies of the BUA with respect to specificity and sensitivity. We can, in general, model our system as shown in FIG. 22. In this figure, Tx (item 222) represents the transmitter (electronics plus transducer); Rx (item 224) represents the receiver (electronics plus transducer). Medium (item 223) is the test material or subject between the transducers. Stimulus (item 221) is the excitation function, often impulse-like. The response h(t) of this system can be written as $$h(t)=h_{St}(t)*h_{Tx}(t)*h_{Medium}(t)*h_{Rx}(t), \qquad (2)$$

where the asterisk [*] represents convolution, and $h_{St}(t)$, $h_{medium}(t)$, $h_{Tx}(t)$, and $h_{Rx}(t)$ are the separate impulse responses associated respectively with the stimulus, transmitter, Medium, and receiver. We deal generally with two types of media:

(1) a calibration medium, such as water; and
(2) a test medium, such as the heel of a human subject.

We then have calibration signals $h_{cal}$ and test signals $h_{test}$, which, in view of equation (1), give us:

$$h_{cal}(t)=h_{St}(t)*h_{Tx}(t)*h_{cal\ medium}(t)*h_{Rx}(t) \qquad (3)$$

$$h_{test}(t)=h_{St}(t)*h_{Tx}(t)*h_{test\ medium}(t)*h_{Rx}(t) \qquad (4)$$

When the calibration medium is water $h_{cal}(t) \approx \delta(t-to)$; that is, the signal undergoes a simple time delay without distortion. Thus, for current purposes, we can deal with $$h_{water}(t)=h_{St}(t)*h_{Tx}(t)*h_{Rx}(t). \qquad (5)$$

Note that any variations in contact between transducer and the test medium are implicitly included in $h_{test}$.

Figure 23A:
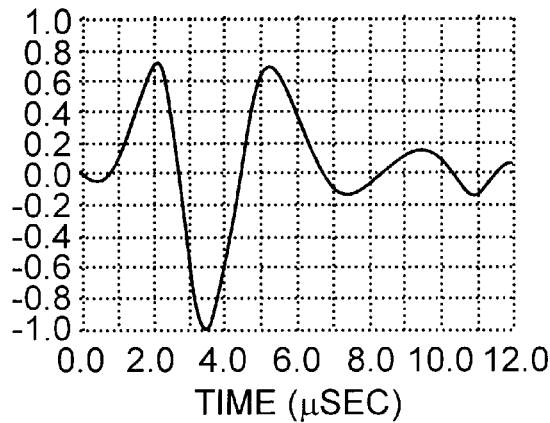
FIGS. 23A–C show a comparison of typical waveform signatures received in cases of healthy bone, osteoporotic bone, and water calibration.
Figure 23B:
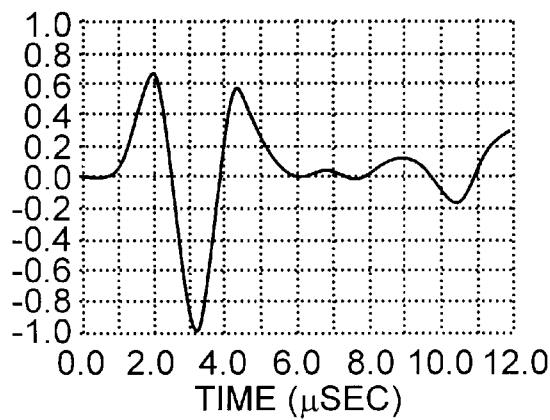
Figure 23C:
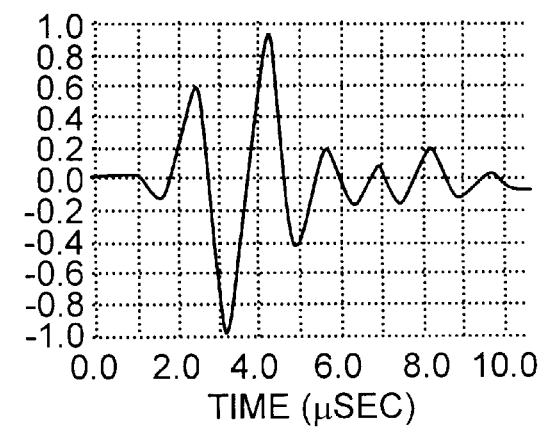

We define a procedure to attempt to derive an estimated value for BUA from a UBI-5c measurement. In this connection, consider wave forms A, B and C in FIGS. 23A–C. Wave form A illustrates a signal that might be obtained from receiver Rx using a healthy bone as part of the Medium. The approximate period of the first cycle or two is ~3–4 microseconds (and ~2–2.5 microseconds for unhealthy bone). Wave form B illustrates a corresponding signal using an osteoporotic bone, showing a shorter first cycle than in wave form A. Wave form C illustrates a typical water calibration signal. The period of the first few cycles is 1–2 microseconds. The measure UBI-5c is derived by estimating the frequency (and period) near the first positive peak (P in figure A).

We derive a BUA estimated value corresponding to the signal A and its UBI-5c as follows. First, assume a family of filters providing responses $h_{filter}(t)$ that are defined by a transfer function $F_m$ having the form $$F_m(f)=Ae^{mf}e^{i\phi(f)} \cdot W(f) \qquad (6)$$

Where:
m represents the (negative) slope of a log-linear amplitude function;
A is a constant;
$\phi(f)$ is a phase transfer function; and
W(f) is a window function that can be added if necessary to adjust for signal processing artifacts (such as ringing). The function $h_{filter}(t)$ may be determined from $F_m(f)$ through a standard Inverse Fourier Transform.

The idea is to find the value of m such that $h_{filter\ system}(t)=h_{Sr}(t)*h_{Tx}(t)*h_{filter}(t)*h_{Rx}(t)$ gives the best fit to the observed subject data in the neighborhood of the first positive peak (point P of wave form A of FIG. 23). This value for m, the slope, corresponds to a BUA value. We can thus define an estimated value of BUA that corresponds to UBI-5(c), which is also determined exclusively by the data near P.

Alternatively, UBI-5c may be computed for the wave form $h_{filter\ system}(t)$ and a UBI-5c value may be associated with the BUA value corresponding to m. Thus, the UBI-5c/BUA correspondence may be incorporated into a look-up table.

The remaining parameters may be chosen in the following manner. A and m may be allowed to vary initially to give the best fit. This may be accomplished, for example, using a two-parameter nonlinear least squares fit. Alternatively, the value for A be fixed and then one may determine the value m(A), then continue until enough values of A have been tried to get a good estimate of the optimum.

Initially $\phi(i)$ will be taken as a constant. This is equivalent to assuming there is no dispersion and that the zero of time is redefined so as to remove the remaining linear phase function associated with a fixed delay from Tx to Rx. Similarly, one may initially set W(f)=1. In the event of interference from deleterious artifacts, one may thereafter establish a suitable window W(f) to reduce the effect of such artifacts.

Note that since $h_{cal\ medium}=\delta(t-t_0)$ as an excellent approximation for water calibration, $$h_{filtered\ system}(t)=h_{cal}(t)*h_{filter}(t).$$

Accordingly, we have shown a method of deriving an estimate of BUA corresponding to a UBI value, utilizing a general system of the type described above, and taking the following steps:

(a) determining the wave forms $h_{subject}(t)$ and $h_{cal}(t)$ resulting respectively from use of the system with a subject and with a calibration medium;

(b) determining the UBI value from $h_{subject}(t)$;

(c) finding the value of m such that $$h_{filter\ system}(t)=h_{filter}(t)*h_{cal}(t)$$

gives the best fit to $h_{subject}(t)$ in a neighborhood of interest, where the response $h_{filter}(t)$ is defined by a transfer function $F_m$ having the form $$F_m(f)=Ae^{mf}e^{j\phi(f)}.W(f)$$

where:
m represents the slope of a log-linear amplitude function:
A is a constant;
$\phi(f)$ is a phase transfer function; and
W(f) is an optional window function; and (d) matching the value m with the UBI value associated with the wave form $h_{subject}(t)$. The BUA can be determined from the value m by appropriate scaling.

This method assumes that the calibration medium, like water, has substantially frequency independent attenuation in a frequency range of interest. However, the method can be readily modified utilizing the relationships outlined above to deal with other calibration media.

What is claimed is:

1. An apparatus for externally determining in a vertebrate subject an index of porosity and non-connectivity of a bone disposed within a body part, the apparatus comprising:
   a. an acoustic transceiver having
      i. a signal generator for producing, when coupled to a transducer, an acoustic pulse, having energy distributed over a frequency range and
      ii. a transducer assembly including a plurality of transducers and providing a pair of transducers in spaced relationship with respect to the bone, wherein a first one of the pair is coupled to the signal generator so as to provide an acoustic pulse and a second one of the pair receives an acoustic signal resulting from propagation of the acoustic pulse along a path that includes the bone, and wherein the assembly is configured so that the path may be disposed in a plurality of positions so as to pass through a plurality of locations within a selected region of the bone;
   b. a signal processor, in communication with the second one of the pair of transducers, for providing a measure, associated with each of the locations, that is indicative of at least one of transient spectral or transient temporal components of a portion, up to the whole amount thereof, of the signal received by the second one of the pair of transducers;
   c. a value memory for storing values related to the measure associated with the locations;
   d. a location processor for identifying a reference location based at least on a local minimum slope magnitude of the measure associated with the locations and selecting a target location having a specified relation to the reference location; and
   e. an output processor for providing as an output a quantity associated with the target location.

2. An apparatus according to claim 1, wherein the quantity is the measure associated with the target location.

3. An apparatus according to claim 1, wherein the quantity is distinct from the measure associated with the target location.

4. An apparatus according to claim 1, wherein the location processor includes means for identifying a reference location based at least in part on the values in the value memory and for selecting the target location based at least in part on the reference location.

5. An apparatus according to claim 1, wherein the location processor has a geometrical data input for defining a default location based on geometry of the body part and the target location is selected by the location processor based on both the geometrical data input and on values stored in the value memory.

6. An apparatus according to claim 5, wherein the location processor includes means for identifying an edge of the bone based on values in the value memory.

7. An apparatus according to claim 6, wherein the location processor includes means for identifying a location of the bone that is set back from the edge of the bone by a specified distance in a specified direction relative to the edge of the bone.

8. An apparatus according to claim 7, wherein the bone is the calcaneus and the location processor includes means for identifying a candidate region, set back from the edge, with respect to which the values in the value memory are relatively insensitive to position.

9. An apparatus for externally determining in a vertebrate subject an index of porosity and non-connectivity of a bone disposed within a body part, the apparatus comprising:

(a) an acoustic transceiver having
   (i) a signal generator for producing, when coupled to a transducer, an acoustic pulse, having energy distributed over a frequency range and
   (ii) a transducer assembly including a plurality of transducers and providing a pair of transducers in spaced relationship with respect to the bone, wherein a first one of the pair is coupled to the signal generator so as to provide an acoustic pulse and a second one of the pair receives an acoustic signal resulting from propagation of the acoustic pulse along a path that includes the bone, and wherein the assembly is configured so that the path may be disposed in a plurality of positions so as to pass through a plurality of locations within a selected region of the bone;
(b) a signal processor, in communication with the second one of the pair of transducers, for providing a measure, associated with each of the locations, that is indicative of at least one of spectral or temporal components of a portion, up to the whole amount thereof, of the signal received by the second one of the pair of transducers;
(c) a value memory for storing values related to the measure associated with the locations;
(d) a location processor for identifying an edge of the bone based on values in the value memory and for selecting a target location based at least in part on the values stored in the value memory; and
(e) an output processor for providing as an output a quantity associated with the target location.

10. An apparatus according to claim 9, wherein the location processor includes means for identifying a location of the bone that is set back from the edge of the bone by a specified distance.

11. An apparatus according to claim 9, wherein the bone is the calcaneus and the location processor includes means for identifying a candidate region, set back from the edge, with respect to which the values in the value memory are relatively insensitive to position and means for selecting the reference location as a function of the default location and a specified location in the candidate region.

12. An apparatus according to claim 9, wherein the location processor includes means for identifying a reference location that is in the candidate region and, if a local trough in measure values is present in the candidate region, in such trough.

13. An apparatus according to claim 9, wherein the location processor includes means for identifying a reference location that is in the candidate region and, if a local trough in measure values is present in the candidate region, in such trough, and wherein the specified location is the reference location.

14. A method for externally determining in a vertebrate subject an index of porosity and non-connectivity of a bone disposed within a body part, the method comprising:

a. providing an apparatus, the apparatus comprising:
   i. an acoustic transceiver having
      a signal generator for producing, when coupled to a transducer, an acoustic pulse, having energy distributed over a frequency range and
      a pair of transducers in spaced relationship with respect to the bone, wherein a first one of the pair is coupled to the signal generator so as to provide an acoustic pulse and a second one of the pair receives an acoustic signal resulting from propagation of the acoustic pulse along a path that includes the bone, and wherein the assembly is configured so that the path may be disposed in a plurality of positions so as to pass through a plurality of locations within a selected region of the bone; and
   ii. a signal processor, in communication with the second one of the pair of transducers, for providing a UBI measure, associated with each of the locations, that is indicative of at least one of spectral or temporal components of a portion, up to the whole amount thereof, of the signal received by the second one of the pair of transducers;
b. storing values related to the UBI measure in a plurality of memory locations wherein each memory location is associated with at least one of the plurality of locations within the selected region of the bone;
c. identifying a reference location based at least on a local minimum slope magnitude of the measure associated with the locations;
d. selecting a target location having a specified relation to the reference location; and
e. providing a quantity characteristic of the porosity of the bone based on at least one UBI measure associated with the target location.

15. A method according to claim 14, further comprising:
(a) identifying the edge of the bone in a coordinate system associated with the transducers; and
(b) defining a reference location with respect to the edge of the bone such that the step of selecting a target location includes selecting a target location based on a specified offset from the reference location.

16. A method for externally determining in a vertebrate subject an index of porosity and non-connectivity of a bone disposed within a body part, the method comprising:

(a) providing an apparatus, the apparatus comprising:
   (i) an acoustic transceiver having
      a signal generator for producing, when coupled to a transducer, an acoustic pulse, having energy distributed over a frequency range and
      a pair of transducers in spaced relationship with respect to the bone, wherein a first one of the pair is coupled to the signal generator so as to provide an acoustic pulse and a second one of the pair receives an acoustic signal resulting from propagation of the acoustic pulse along a path that includes the bone, and wherein the assembly is configured so that the path may be disposed in a plurality of positions so as to pass through a plurality of locations within a selected region of the bone;
   (ii) a signal processor, in communication with the second one of the pair of transducers, for providing a UBI measure, associated with each of the locations, that is indicative of at least one of spectral or temporal components of a portion, up to the whole amount thereof, of the signal received by the second one of the pair of transducers;
(b) storing values related to the UBI measure in a plurality of memory locations wherein each memory location is associated with at least one of the plurality of locations within the selected region of the bone; and
(c) providing a quantity characteristic of the porosity of the bone based on at least a topological signature of a spatial distribution of a UBI measure in the selected region of the bone.

17. A method for characterizing a propensity of a subject to change of porosity of bone, the method comprising:
(a) providing an apparatus, the apparatus comprising:
　i. an acoustic transceiver having
　　a signal generator for producing, when coupled to a transducer, an acoustic pulse, having energy distributed over a frequency range and
　　a pair of transducers in spaced relationship with respect to the bone, wherein a first one of the pair is coupled to the signal generator so as to provide an acoustic pulse and a second one of the pair receives an acoustic signal resulting from propagation of the acoustic pulse along a path that includes the bone, and wherein the assembly is configured so that the path may be disposed in a plurality of positions so as to pass through a plurality of locations within a selected region of the bone; and
　ii. a signal processor, in communication with the second one of the pair of transducers, for providing a UBI measure, associated with each of the locations, that is indicative of at least one of spectral or temporal components of a portion, up to the whole amount thereof, of the signal received by the second one of the pair of transducers;
b) storing values related to the UBI measure in a plurality of memory locations wherein each memory location is associated with at least one of the plurality of locations within the selected region of the bone; and
c) providing a quantity characteristic of the propensity of a subject to change of porosity of bone based on at least a topological signature of a spatial distribution of a UBI measure in the selected region of the bone.

18. An apparatus for externally determining in a vertebrate subject an index of porosity and non-connectivity of a bone disposed within a body part, the apparatus comprising:
a. an acoustic transceiver having
　i. a signal generator for producing, when coupled to a transducer, an acoustic pulse, having energy distributed over a frequency range and
　ii. a transducer assembly including a plurality of transducers and providing a pair of transducers in spaced relationship with respect to the bone, wherein a first one of the pair is coupled to the signal generator so as to provide an acoustic pulse and a second one of the pair receives an acoustic signal resulting from propagation of the acoustic pulse along a path that includes the bone, and wherein the assembly is configured so that the path may be disposed in a plurality of positions so as to pass through a plurality of locations within a selected region of the bone;
b. a signal processor, in communication with the second one of the pair of transducers, for providing a measure, associated with each of the locations, that is indicative of at least one of transient spectral or transient temporal components of a portion, up to the whole amount thereof, of the signal received by the second one of the pair of transducers;
c. a value memory for storing values related to the measure associated with the locations;
d. a location processor for identifying an edge of the bone based on values in the value memory and for selecting a target location having a specified relation to the edge of the bone; and
e. an output processor for providing as an output a quantity associated with the target location.

19. An apparatus according to claim 18, wherein the location processor includes means for identifying a location of the bone that is set back from the edge of the bone by a specified distance in a specified direction relative to the edge of the bone.

20. An apparatus according to claim 19, wherein the bone is the calcaneus and the location processor includes means for identifying a candidate region, set back from the edge, with respect to which the values in the value memory are relatively insensitive to position.

\* \* \* \* \*